(12) United States Patent
Ho et al.

(10) Patent No.: US 9,103,719 B1
(45) Date of Patent: *Aug. 11, 2015

(54) COMPUTATION OF GLINT, GLARE, AND SOLAR IRRADIANCE DISTRIBUTION

(75) Inventors: Clifford Kuofei Ho, Albuquerque, NM (US); Siri Sahib Singh Khalsa, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 1027 days.

This patent is subject to a terminal disclaimer.

(21) Appl. No.: 13/106,686

(22) Filed: May 12, 2011

(51) Int. Cl.
*G01J 1/20* (2006.01)
*G01J 1/16* (2006.01)
*G01J 1/42* (2006.01)

(52) U.S. Cl.
CPC ........ *G01J 1/1626* (2013.01); *G01J 2001/4266* (2013.01); *Y02E 10/40* (2013.01)

(58) Field of Classification Search
CPC ............... F24J 2/38; F24J 2/40; F24J 2/407; F24J 2200/04; Y02E 10/40; Y02E 10/41; Y02E 10/42; Y02E 10/52; G01W 1/10; G01J 1/1626; G01J 2001/4266
USPC ......... 250/208.1, 203.3, 203.4; 356/445, 446, 356/448; 348/135; 353/3; 126/573, 574, 126/578, 600, 601
See application file for complete search history.

(56) References Cited

U.S. PATENT DOCUMENTS 5,353,055 A * 10/1994 Hiramatsu .................... 348/145
5,659,168 A * 8/1997 Dey et al. .................... 250/208.1
7,906,750 B2 * 3/2011 Hickerson et al. ......... 250/203.4
8,669,509 B1 * 3/2014 Gupta et al. ............... 250/203.4
2010/0006087 A1   1/2010 Gilon et al.
2013/0152997 A1 * 6/2013 Yao et al. ...................... 136/246

OTHER PUBLICATIONS

Mavis, C.L., 1988, "10 MWe Solar Thermal Central Receiver Pilot Plant Heliostat and Beam Characterization System Evaluation Nov. 1981-Dec. 1986," SAND87-8003, Sandia National Laboratories, Livermore CA, pp. 1-218, May 1988.

Strachan, J.W. and R.M. Houser, 1993, "Testing and Evaluation of Large Area Heliostats for Solar Thermal Applications," SAND92-1381, Sandia National Laboratories, Albuquerque, NM, pp. 1-70, Feb. 1993.

Blackmon, J.B., 1985, "Development and Performance of a Digital Image Radiometer for Heliostat Evaluation at Solar One," J. Solar Energy Engr., 107, pp. 315-321, Nov. 1985.

Johnston, G., 1998, "Focal Region Measurements of the 20 m2 Tiled Dish at the Australian National University," Solar Energy, 63(2), pp. 117-124.

(Continued)

*Primary Examiner* — John Lee
(74) *Attorney, Agent, or Firm* — Daniel J. Jenkins

(57) ABSTRACT

Described herein are technologies pertaining to computing the solar irradiance distribution on a surface of a receiver in a concentrating solar power system or glint/glare emitted from a reflective entity. At least one camera captures images of the Sun and the entity of interest, wherein the images have pluralities of pixels having respective pluralities of intensity values. Based upon the intensity values of the pixels in the respective images, the solar irradiance distribution on the surface of the entity or glint/glare corresponding to the entity is computed.

12 Claims, 16 Drawing Sheets

(56) References Cited

OTHER PUBLICATIONS

Ulmer, S., W. Reinalter, P. Heller, E. Lupfert, and D. Martinez, 2002, "Beam Characterization and Improvement with a Flux Mapping System for Dish Concentrators," J. Solar Energy Engr., 124, pp. 182-188, May 2002.

Slack, M., P. Meduri, and A. Sonn, 2010, "eSolar Power Tower Performance Modeling and Experimental Validation," in Proceedings of SolarPACES 2010, Perpignan, France, Sep. 21-24, 2010, pp. 1-8.

Yogev, O., P. Gleckman, and M. Rozler, 2009, "High-Heat Solar Flux Scanner," in Proceedings of SolarPACES 2009, Berlin, Germany, Sep. 15-18, 2009, pp. 1-8.

Naor, G., G. Goldwine, R. Hayut, O. Bibi, E. Silberstein, O. Chernin, Z. Auman, G. Kroyzer, and A. Ziskin, 2010, "Flux Measurement System Using IR Camera," in Proceedings of SolarPACES 2010, Perpignan, France, Sep. 21-24, 2010, pp. 1-6.

* cited by examiner

COMPUTATION OF GLINT, GLARE, AND SOLAR IRRADIANCE DISTRIBUTION

STATEMENT OF GOVERNMENTAL INTEREST

This invention was developed under contract DE-AC04-94AL85000 between Sandia Corporation and the U.S. Department of Energy. The U.S. Government has certain rights in this invention.

BACKGROUND

Due to environmental concerns pertaining to the use of fossil fuels in connection with generating electric power, including the non-renewability of such fossil fuels and carbon emissions and other pollutants generated when fossil fuels are burned, an increasing amount of research and funding has been directed towards systems that utilize renewable energy sources to generate electric power. These systems include solar power plants, wind turbines, geothermal power systems, and the like. An exemplary solar power system is a solar power tower (which can also be referred to as a central tower power plant, a heliostat power plant, or a power tower). A solar power tower utilizes an elevated central receiver to collect focused solar radiation from a plurality of reflectors (also referred to as collectors), such as heliostats. Solar radiation is reflected from the reflectors and concentrated at the central receiver, where a fluid is heated. The heating of the fluid can cause a turbine to be driven to generate electric power. Problems can arise, however, when the concentrated solar radiation is not relatively uniformly distributed across the surface of the central receiver. For instance, "hot spots" are undesirable on the surface of the central receiver, as damage to the central receiver may occur if too much solar radiation is concentrated at any one portion of the central receiver.

Several techniques have been developed that are utilized to measure irradiance on the surface of a central receiver of a solar power tower. An exemplary conventional method requires the use of a water-cooled flux gauge or calorimeter (a sensor) that is affixed to the surface of the central receiver. This sensor is employed to obtain a measurement of irradiance at the location of the sensor. An electronic image of the surface of the central receiver can then be captured, and intensity values of pixels of the image can be calibrated based at least in part upon irradiance measured by the sensor. This approach, however, requires the utilization of the aforementioned sensor, which can be relatively expensive and difficult to calibrate.

Another conventional approach utilizes a CCD camera to measure the irradiance distribution on the surface of the receiver from a dish concentrator. Instead of using a flux gauge or calorimeter, however, the total power from the dish collector is calculated and utilized to calibrate pixel values of an image captured by way of the CCD camera. This approach requires that an entirety of a beam is captured by the receiver. In operation, a solar power tower can be surrounded by hundreds or thousands of reflectors—therefore, it is impractical to expect no spillage of concentrated light outside of the surface area of the central receiver.

Yet another exemplary conventional approach for computing an irradiance distribution across the surface of a central receiver is the utilization of a flux scanner that can measure their radiance distribution from an entire heliostat field. A flux scanner comprises flux sensors that are included in a long wand that is configured to rotate in front of the central receiver. A remote video camera is used to capture images of the reflected irradiance from the wand as such wand is rotated, and the sensors in the wand are used to calibrate pixel values corresponding to the Lambertian surface of the wand. The resulting recorded images of the wand while rotated in front of the receiver are stitched together to yield a flux map of the irradiance distribution at the aperture of the central receiver line.

Yet another exemplary conventional approach for determining irradiance distribution across the surface of a central receiver of a solar power tower includes the use of a flux measurement system that comprises an infrared camera that measures the surface temperature of the central receiver, and the irradiance distribution across such receiver can be inferred based upon the surface temperature. Utilizing this approach, many processes and parameters must be known to calculate the irradiance distribution across the surface of the central receiver. These include the thermodynamic properties of the fluid that is to be heated, properties of the materials of the central receiver, and heat loss due to radiation and convection. Uncertainty in these parameters and processes and associated parameters that impact these processes, such as ambient temperature and wind speed, can contribute to uncertainties in the calculated irradiance distribution.

Furthermore, as mentioned above, solar receivers are generally surrounded by numerous reflectors (heliostats, mirrored troughs, or dish concentrator facets). From certain perspectives, this reflection of solar radiation can result in an unintended side effect: solar glare. Assessment of the potential hazards of glint and glare from concentrating solar power plants is an important requirement to ensure public safety. Glint can be defined herein as a momentary flash of light, while glare is defined as a more continuous source of excessive brightness relative to the ambient lighting. There is currently no cost effective solution in place to obtain a measure of glint or glare caused by reflectors, receivers, or other components utilized in concentrating solar power systems such as power tower systems, linear concentrator systems (e.g., parabolic troughs or linear Fresnel) and dish/engine systems.

SUMMARY

The following is a brief summary of subject matter that is described in greater detail herein. This summary is not intended to be limiting as to the scope of the claims.

Described herein are various technologies pertaining to computing a solar irradiance distribution across a surface area of a receiver in a solar power tower or other concentrating solar power system. Additionally, described herein are various technologies pertaining to computing a metric that is indicative of glint and/or glare emitted from an entity such as a heliostat, a heliostat field, a mirrored trough, a mirrored trough field, a dish concentrator, a receiver, a window, or the like. With more particularity, a solar irradiance distribution across the surface area of a receiver can be computed free of the utilization of one or more sensors applied to the surface of the receiver. Instead, the solar irradiance distribution can be computed through utilization of an electronic image of the receiver in the concentrating solar power system and an electronic image of the Sun.

Electromagnetic radiation that is emitted from the Sun is reflected off of numerous reflective entities, such as heliostats, and concentrated at a receiver, such as a central receiver on the solar power tower. A camera, which may be a video camera or still camera, can be employed to capture an electronic image of the Sun, wherein the electronic image of the Sun has a plurality of pixels that have a plurality of intensity values. Pursuant to an example, to avoid saturation of pixel values, a filter can be employed to attenuate light received at the lens of the camera. This filter may be a physical filter that can attenuate light captured by the digital camera, or may be an electronic filter that performs such attenuation. The digital camera (or another digital camera) can be employed to capture an image of the receiver as solar radiation is concentrated onto the receiver by the reflective entities. Again, a filter that is substantially similar to the filter utilized when capturing the electronic image of the Sun can be employed when capturing the electronic image of the receiver that is receiving concentrated solar radiation. The image of the receiver that receives the concentrated solar radiation also comprises a plurality of pixels that have a corresponding plurality of intensity values. An irradiance distribution on the surface of the receiver can be computed for locations of the receiver that are captured by pixels in the electronic image of the receiver.

Accordingly, a solar irradiance distribution across the surface of the receiver can be computed, and this irradiance distribution can be utilized to identify "hot spots" on the surface of the receiver. A hotspot can indicate locations on the receiver where solar radiation is more highly concentrated than at other locations on the surface of the receiver. Again, this solar irradiance distribution can be computed based at least in part upon pixel values of the electronic image of the Sun and pixel values of the electronic image of the receiver in the concentrating solar power system.

With more specificity, one or more digital cameras may be configured to capture respective images of the Sun and of the receiver. Additionally, a value for a direct normal irradiance at a time that the electronic image of the Sun was captured can be obtained, for instance, from a measurement device at the solar power tower. Furthermore, image analysis techniques can be utilized to compute a radius of the Sun in pixels as captured in the electronic image of the Sun. In another exemplary embodiment, a human can identify a center of the Sun in the electronic image of the Sun as well as an edge of the Sun, and a number of pixels between the center of the Sun and the edge of the Sun in the electronic image of the Sun can be identified. Moreover, a value of reflectivity of the receiver can be computed, estimated, or otherwise received. Furthermore, the angle subtended by the Sun can be received, and the irradiation on the receiver captured by pixels in the electronic image of the receiver can be computed based at least in part upon the values of the pixels in the electronic image of the receiver and the electronic image of the Sun as well as the aforementioned other parameters. Furthermore, these pixels can be mapped to physical space corresponding to the receiver.

Additionally, similar techniques can be utilized in connection with computing values for glint and/or glare emitted from a reflective source, such as a heliostat field, a mirrored trough field or other suitable reflective source. One or more digital cameras can be utilized to capture an image of the Sun as well as an image of the reflective entity that reflects solar radiation received from the Sun. An amount of power per unit area emitted by the Sun can be known and can be correlated to the pixels in the image of the Sun. Pixel values in the image of the Sun can be summed and translated such that the pixel values correspond to an amount of power per unit area (Watts/m$^2$). Pixel values in the image of the reflective entity may also be summed and can be scaled against the pixel values in the captured image of the Sun. In other words, based at least in part upon the values of the pixels in the image of the Sun and the values of the pixels in the image of the reflective entity, an amount of power per unit solid angle emitted from the reflective entity can be computed. Thereafter, an amount of power that is received through the pupil of an eye of an individual can be computed based at least in part upon a known size of the pupil and the amount of power per unit solid angle emitted from the reflective entity. This value of power received at a human eye is indicative of an amount of glint or glare caused by solar reflection from the reflective entity.

Other aspects will be appreciated upon reading and understanding the attached Figs. and description.

DETAILED DESCRIPTION

Figure 1:
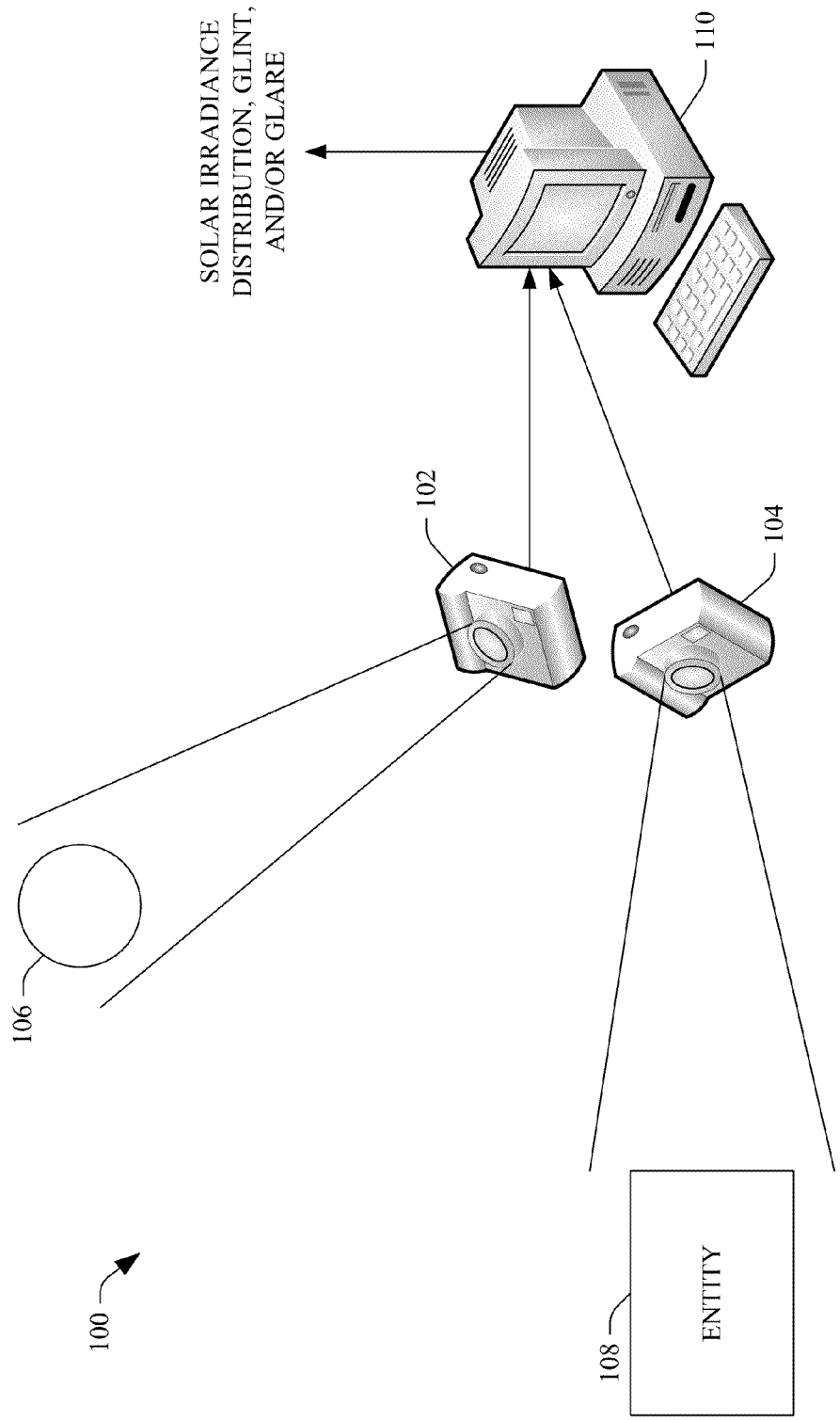
FIG. 1 illustrates a system that facilitates computing one of solar irradiance distribution across the surface of a receiver in a concentrating solar power system or glint and/or glare emitted from a reflective entity.

Various technologies pertaining to computing an irradiance distribution across the surface of a receiver of a concentrating solar power system as well as various technologies pertaining to computing glint and/or glare emitted from a reflective entity will now be described with reference to the drawings, where like reference numerals represent like elements throughout. In addition, several functional block diagrams of exemplary systems are illustrated and described herein for purposes of explanation; however, it is to be understood that functionality that is described as being carried out by certain modules may be performed by multiple modules. Additionally, as used herein, the term "exemplary" is intended to mean serving as an illustration or example of something, and is not intended to indicate a preference.

With reference now to FIG. 1, an exemplary system 100 that facilitates computing at least one of solar irradiance distribution across a receiver or glint and/or glare emitted from a reflective entity is illustrated. The system 100 comprises a first camera 102 and a second camera 104. The first and second cameras 102 and 104 are digital cameras that capture images in electronic format. Pursuant to an example, the cameras 102 and 104 may be CCD cameras, CMOS cameras, or other suitable cameras in which the pixel value scales linearly with the received irradiance. Furthermore, the cameras 102 and 104 may be cameras that are configured to capture still pictures and/or cameras that are configured to capture video. In an exemplary embodiment, at least one of the cameras 102 or 104 may be included in a portable computing device, such as a portable telephone, a portable media player, a tablet computing device, or the like. Additionally, both cameras 102 and 104 may be included in a portable computing device such that the camera 102 is configured to point in a first direction and the camera 104 is configured to point in a second direction. Alternatively, rather than utilizing two cameras, a single one of the cameras 102 or 104 can be employed as will be described below.

The first camera 102 can be positioned to capture an image of the Sun 106. Accordingly, the first camera 102 can generate an electronic image of the Sun 106 that comprises a plurality of pixels that have a plurality of intensity values corresponding thereto. To avoid saturating the pixel values, a filter can be utilized in connection with the first camera 102 to attenuate light captured by the first digital camera 102 when pointed at the Sun 106. For instance, the filter may be a material that is placed over the lens of the first digital camera 102. Additionally or alternatively, the first digital camera 102 can have an electronic filter corresponding thereto that electronically attenuates light captured by the first camera 102 when capturing an image of the Sun 106.

The system 100 may further comprise a second camera 104 that is pointed at an entity 108. For instance, the entity 108 may be a receiver in a solar power tower. In another example, the entity 108 may be a heliostat, a plurality of heliostats, a mirrored trough, a plurality of mirror troughs, or some other reflective entity. While several examples are provided herein that describe the entity 108 as being a central receiver in a solar power tower, it is to be understood that the entity 108 may be any suitable receiver that can be utilized in any suitable concentrating solar power system, and the examples are not intended to limit the scope of the claims. The second digital camera 104 can also utilize a filter (similar to the filter utilized by the first digital camera 102 when capturing the image of the Sun 106) when capturing the digital image of the entity 108. In another example, the second digital camera 104 may utilize a filter that is different from the filter used by the first digital camera 102, where differences between the filters are known (e.g., differences in magnitude of attenuation can be known). Additionally, the first digital camera 102 and the second digital camera 104 may have identical settings (zoom, shutter speed, resolution, etc.) when capturing the images of the Sun 106 and the entity 108, respectively. The electronic image of the entity 108 comprises a plurality of pixels that have a plurality of intensity values corresponding thereto.

The system 100 additionally comprises a computing apparatus 110 that receives the electronic image of the Sun 106 generated by the first digital camera 102 and the electronic image of the entity 108 generated by the second digital camera 104, and computes at least one of solar irradiance distribution across the surface of the entity 108 or glint and/or glare emitted from the entity 108 based at least in part upon the values of the pixels of the received electronic images. In other words, the computing device 110 can include computer-executable instructions that can cause an irradiance distribution across the surface of the entity 108 and/or glare/glint emitted from the entity 108 to be computed based at least in part upon pixel values of the image of the Sun and the image of the entity 108, respectively. Additional detail pertaining to the instructions that may be included in the computing device 110 will be provided below.

As mentioned above, while the system 100 shows the two digital cameras 102 and 104, it is to be understood that the system 100 may comprise a single digital camera. For instance, the system 100 may comprise the digital camera 102 but not the digital camera 104. In such an embodiment, the first digital camera 102 can be positioned to capture an electronic image of the Sun 106 and may thereafter be positioned to capture an electronic image of the entity 108. Alternatively, the image of the Sun may be captured at a previous point in time and utilized numerous times in connection with computing irradiance distribution across the surface of the entity 108 and/or glint/glare emitted from the entity 108.

In another exemplary embodiment, the first digital camera 102 may be a video camera that is positioned on a mechanism that causes the first digital camera 102 to track the position of the Sun 106 as the Sun crosses the sky. The second digital camera 104 may also be a video camera that is configured to continuously capture video of the entity 108. The computing device 110 can receive video from the first digital camera 102 and the second digital camera 104 and can periodically or on demand compute at least one of the solar irradiance distribution across the surface of the entity 108 or the glint and/or glare emitted from the entity 108.

In still yet another exemplary embodiment, the computing device 110 may comprise at least one of these digital cameras 102 or 104. For instance, the computing device 110 may be a mobile telephone, a mobile media device, a mobile gaming console, a tablet computing device, or some other mobile computing device that includes at least one camera. The mobile computing device may be positioned such that the camera therein captures an image of the Sun 106 and may thereafter be repositioned such that the camera captures an image of the entity 108. The mobile computing device 110 may then compute the solar irradiance distribution across the surface of the entity 108 or the glint and/or glare emitted from the entity 108 based at least in part upon the values of pixels of the electronic images of the Sun 106 and the entity 108 captured by the mobile computing device.

In still yet another exemplary embodiment, the computing device 110 may be a mobile computing device that comprises both the first digital camera 102 and the second digital camera 104, wherein positions of the digital camera 102 and 104 are alterable relative to one another. Accordingly, the mobile computing device 110 can cause the first digital camera 102 to capture an image of the Sun 106 while the second digital camera 104 substantially simultaneously captures an electronic image of the entity 108. The computing device 110 may then compute one of the solar irradiance distribution across the surface of the entity 108 or the glint and/or glare emitted from the entity 108 based at least in part upon the values of pixels in the images captured by the first digital camera 102 and the second digital camera 104.

In another exemplary embodiment, the computing device 110 may be in communication with the digital cameras 102 and/or 104 by way of a local area network. Thus, for example, the first digital camera 102 and/or the second digital camera 104 (if the system 100 comprises both digital cameras 102 and 104) can comprise wireless antennas that are utilized to wirelessly transmit images to the computing device 110 (or an intermediate computing device in communication with the computing device 110). Responsive to receipt of the electronic images, the computing device 110 can compute one of the solar irradiance distribution across the surface of the entity 108 or the glint and/or glare emitted from the entity 108 based at least in part upon the pixel values in the electronic images captured by the first digital camera 102 and the second digital camera 104.

In still yet another exemplary embodiment, the electronic images of the Sun 106 and the entity 108 can be uploaded to the computing device 110, which can have a browser executing thereon. The user of the computing device 110 may then utilize a browser to access a web-based service that facilitates performing the computation of the one of solar irradiance distribution across the surface of the entity 108 and/or the glint and/or glare emitted from the entity 108. Alternatively, the digital cameras 102 and 104 may be included in a device that comprises a client-side application that can communicate with a web-based service that is configured to receive the image of the Sun 106 and the image of the entity 108 and compute the solar irradiance distribution across the surface of the entity 108 or the glint and/or glare emitted from the entity 108. Other architectures that facilitate computing the solar irradiance distribution across the surface of the entity 108 and/or the glint and/or glare emitted from the entity 108 are contemplated by the inventors and are intended to fall under the scope of the hereto appended claims.

Figure 2:
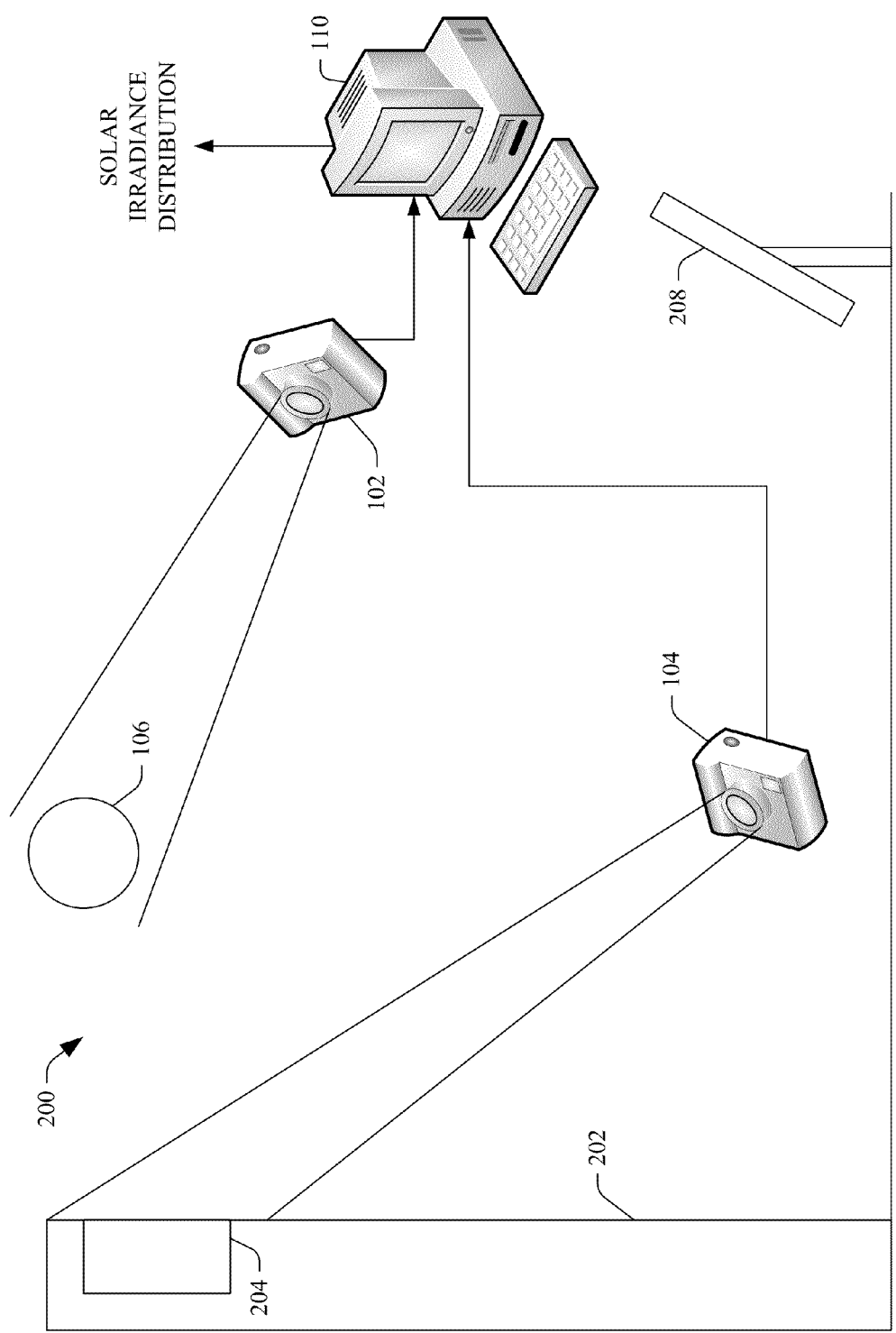
FIG. 2 illustrates a system that facilitates computing a solar irradiance distribution across the surface of a central receiver of a solar power tower.

With reference now to FIG. 2, an exemplary system 200 that facilitates computing solar irradiance distribution across a surface of a central receiver on a solar power tower is illustrated. The system 200 comprises a solar power tower 202 that comprises a central receiver 204. The central receiver 204 is configured to receive concentrated solar radiation from a plurality of reflective entities. Accordingly, the system 200 may comprise a heliostat 208 that reflects radiation emitted from the Sun to concentrate the solar radiation at the central receiver 204. Pursuant to an example, the central receiver 204 can be surrounded by a plurality of reflective entities such as heliostats, mirrored troughs or the like. These reflective entities can be positioned such that they each reflect solar radiation received from the Sun 106 and concentrate such solar radiation at the central receiver 204. A shape of the central receiver 204 may be arbitrary (planar, cylindrical, etc.).

As described above, the first digital camera 102 can capture an electronic image of the Sun 106 and the second digital camera 104 can capture an electronic image of the central receiver 204 as the central receiver 204 is irradiated with concentrated radiation from the heliostat 208 (and/or other reflectors). The computing device 110 can compute a solar irradiance distribution across the surface of the central receiver 204 based at least in part upon values of the pixels of the images captured by the digital cameras 102 and 104. In addition to receiving the electronic images from the digital cameras 102 and 104, the computing device 110 can additionally receive a direct normal irradiance (DNI) corresponding to the Sun 106 at a time when the electronic image of the Sun 106 was captured. For instance, this DNI can be obtained through utilization of a sensor that is proximate to the solar power tower 202. In addition, the computing device 110 can be configured to perform image analysis on the image of the Sun 106 captured by the first digital camera 102 to ascertain a radius of the Sun in pixels. Still further, the computing device 110 can receive data that is indicative of reflectivity of the central receiver 204 across the surface of the central receiver 204. This data that is indicative of reflectivity can be estimated based upon properties corresponding to materials of the central receiver 204 and/or can be computed through utilization of images captured by the first digital camera 102 and the second digital camera 104 as will be described in greater detail below. Additionally, the computing device 110 can receive an angle at the iris of the first digital camera 102 that is subtended by the Sun 106. Based at least in part upon these parameters, the computing device 110 can compute the solar irradiance distribution across the surface of the central receiver 204.

With more particularity, the computing device 110 can be configured to compute, for each pixel in the electronic image of the central receiver 204 captured by the second camera 104, an irradiance value on the surface of the central receiver 204 at such respective pixels. Thereafter, if desired, the pixels can be mapped to spatial regions on the surface of the collector 204 based at least in part upon an angle of the second camera 104 with respect to the central receiver 204 as well as shape of the central receiver 204. An irradiance distribution map corresponding to the surface of the central receiver 204 can then be generated and, for instance, visualized to a user. Gradients of values in the solar irradiance distribution across the surface of the central receiver 204 can be analyzed to locate a nonuniformity of irradiance across the surface of the central receiver 204. This can indicate the existence of "hot spots" that may exist on the surface of the central receiver 204. Existence of a "hot spot" on the surface of the central receiver 204 can indicate that some diagnostic systems are desirably executed with respect to re-aligning one or more concentrators.

Additional detail pertaining to the computing of the solar irradiance distribution across the surface of the central receiver 204 is now provided. An image of the Sun 106 captured by the first digital camera 102 can be utilized to calibrate both the magnitude of a pixel value and a subtended angle of each pixel. For instance, neutral density filters can be applied to the camera lens of the first digital camera 102 to prevent saturation of, for example, the CCD of a CCD camera during exposure. Reference images of the Sun 106 captured by the digital camera 102 can serve two purposes: 1) to provide a quantified irradiance reference so that pixel values can be scaled to power (Watts) using a measured DNI; and 2) to provide a spatial reference to quantify the subtended angle (and size) of the physical image. The subtended angle of the Sun is approximately 9.4 mrad. So long as the zoom of the second camera 104 is held as being the same as the first camera 102 (or the zoom is held constant if the first digital camera 102 is utilized to capture both the image of the Sun 106 and the image of the central receiver 204), then the subtended angle of other images can be obtained by comparison to the image of the Sun captured by the first digital camera 102.

Figure 3:
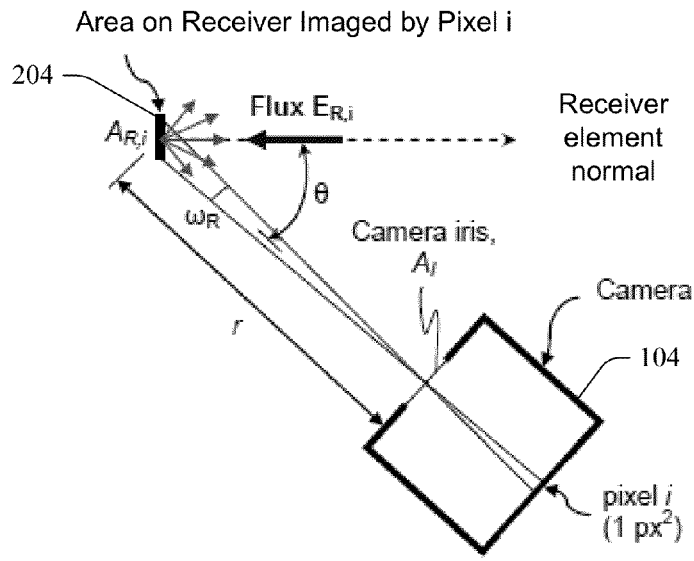
FIG. 3 illustrates a reflection of irradiance on a portion of a diffusely-reflecting receiver as captured by a digital camera.

Details pertaining to pixel conversion utilizing Sun calibration will now be provided. Referring briefly to FIG. 3, a reflection of irradiance on a relatively small portion of a diffuse receiver (e.g., the central receiver 204) towards the second digital camera 104 is illustrated. A pixel i on a raw grayscale image of the central receiver 204 captures an elemental portion of the central receiver 204, $A_{R,i}$ [m$^2$], which can receive an irradiance $E_{R,i}$ [W/m$^2$] from a heliostat field or other concentrator. For instance, the central receiver 204 can be assumed to be a Lambertian (diffuse) reflector with a reflectivity of $\rho_{R,i}$.

Figure 4:
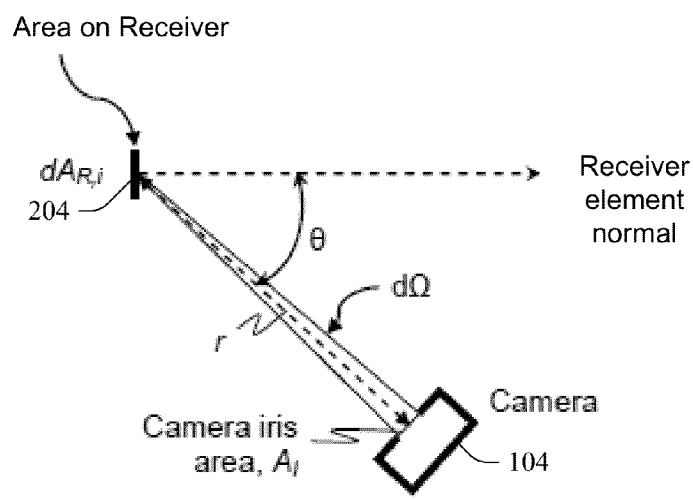
FIG. 4 illustrates a solid angle subtended by a camera iris pointed at a receiver of a concentrating solar power system.

In a CCD camera, the CCD response due to irradiance at this pixel can be expressed in arbitrary voltage units per pixel area $V_{CCD,i}$ [volts/px$^2$], where volts represents the pixel value, and px denotes the unit length of a pixel. As described herein, this recorded signal $V_{CCD,i}$ can be converted to irradiance $E_{R,i}$ [W/m$^2$] incident on the surface of the central receiver 204 $A_{R,i}$ [m$^2$] imaged by the pixel i. An equation for the irradiance at pixel i can be derived by first considering the irradiance incident on the CCD. By definition, the radiant intensity [W/sr] from a diffuse reflection is directly proportional to the cosine of the angle between the surface normal and the line of sight of the camera. Accordingly, the irradiance on the pixel $E_{CCD\_W}$ [W/px$^2$] is given by the following algorithm:

$$E_{CCD\_W} = \frac{I_N \cos(\theta) d\Omega}{1 px^2}, \quad (1)$$

where $I_N$ is the radiant intensity reflected normal to the central receiver 204, $\theta$ is the angle between the surface normal of the central receiver 204 and the camera, $d\Omega$ is the solid angle subtended by the camera iris at the central receiver 204, and px is the unit length of a square pixel. These parameters are illustrated with respect to the second camera 104 and the surface of the central receiver 204 in FIG. 4.

The radiant intensity in the normal direction $I_N$ in Eq. (1) is calculated by noting that all power reflected by surface $A_R$ is reflected into a hemisphere, where $\phi$ is the zenith angle and $\alpha$ is the azimuth angle:

$$\rho_{R,i} E_{R,i} A_{R,i} = \int\int_{Hemisphere} I_N \cos(\theta) d\Omega \quad (2)$$
$$= I_N \int_0^{2\pi} \int_0^{\pi/2} \cos(\theta) \sin(\theta) d\theta d\phi$$
$$= \pi I_N$$
$$\Rightarrow I_N = \frac{\rho_{R,i} E_{R,i} A_{R,i}}{\pi}$$

The solid angle $d\Omega$ in Eq. (1) can be determined assuming that the radius of the iris of the camera 104 is small compared to r[m], which is the distance between the central receiver 204 and the camera 104:

$$d\Omega(sr) = \frac{A_I(m^2)}{r^2(m^2)} \quad (3)$$

where $A_I$[m$^2$] is the area of the iris of the camera 104. Substituting Eq. (2) and Eq. (3) into Eq. (1) yields the following equation for the pixel irradiance [W/px$^2$]:

$$E_{CCD\_W} = \frac{\rho_{R,i} E_{R,i} A_{R,i} \cos(\theta) A_I}{\pi r^2 (1 px^2)}. \quad (4)$$

The pixel irradiance in Eq. (4) can be expressed in terms of the CCD response, $V_{CCD,i}$ [volts/px$^2$] by using a conversion factor between watts and volts. In order to obtain the conversion factor between watts and volts, the image of the Sun 106 is captured through utilization of the first camera 102 using the same zoom and f-stop that was utilized to capture the image of the central receiver 204. Again, the same camera can be employed to capture both the image of the Sun and the image of the central receiver 204. The watts to volt ratio is equal to the ratio of the power that entered the camera in the image of the Sun to the sum of the pixel values within the Sun image:

$$\frac{W}{volt} = \frac{E_{DNI} A_I}{\sum_{sun} V_{CCD\_sun,i}}, \quad (5)$$

where $E_{DNI}$ [W/m$^2$] is the direct normal irradiance at the time the image of the Sun 106 was recorded, $A_I$ [m$^2$] is the area of the iris of the camera, and $V_{CCD\_sun,i}$ is the CCD value of pixel i in the image of the Sun 106. Dividing Eq. (4) by Eq. (5) can yield the following algorithm for the CCD response, $V_{CCD,i}$ [volts/px$^2$]:

$$V_{CCD,i} = \frac{\rho_{R,i} E_{R,i} A_{R,i} \cos(\theta)}{\pi r^2 (1 px^2)} \frac{\sum_{sun} V_{CCD\_sun,i}}{E_{DNI}} \quad (6)$$

Figure 5:
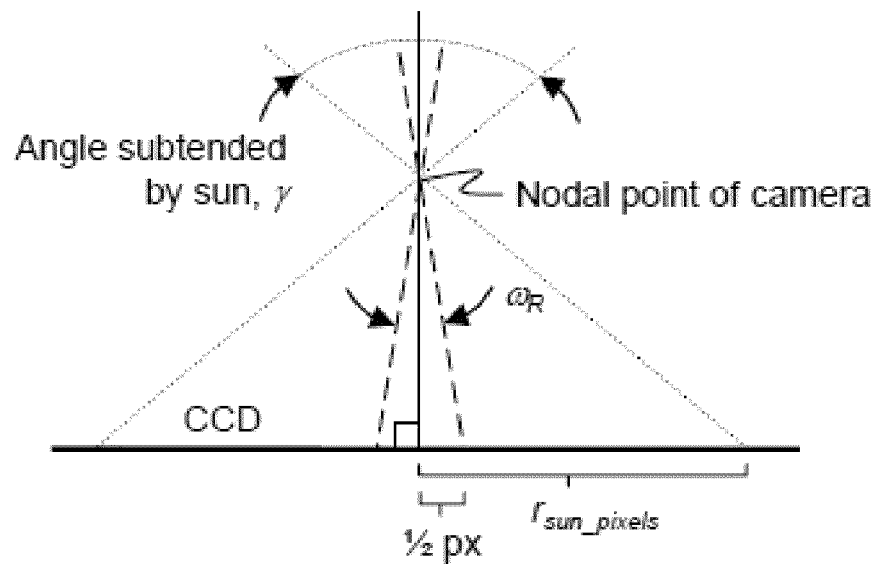
FIG. 5 illustrates the angles subtended by the sun and by one pixel on the CCD of a camera

The central receiver 204 element area $A_{R,i}$ [m] in Eq. (6) can be expressed as follows (refer to FIG. 3):

$$A_{R,i} \cos(\theta) = 4r^2 \tan^2(\omega_R/2), \quad (7)$$

where r [m] is the distance between the central receiver 204 and the camera iris, $\theta$ [rad] is the angle between the surface normal of the central receiver 204 and the camera line of sight, and $\omega_R$ is the angle subtended by $A_{R,i}$ at the camera iris (and spanned by one pixel). If it is assumed that the focal length (zoom) between the nodal point of the camera and the CCD is held constant, an expression for $\omega_R$ can be determined by using the image of the Sun 106 as a reference for images/angles projected between the nodal point and the CCD.

$$\frac{\tan(\frac{\omega_R}{2})}{\frac{1}{2}px} = \frac{\tan(\frac{\gamma}{2})}{r_{sun\_pixels}}, \quad (8)$$

where $r_{sun\_pixels}$ is the number of CCD pixels along the radius of the Sun image and $\gamma$ is the angle subtended by the Sun (approximately 0.0094 rad). These parameters are illustrated in FIG. 5.

Combining Eqs. (6)-(8) can yield the following algorithm for the irradiance on a receiver element, $E_{R,i}$ [W/m$^2$], as a function of each pixel value, $V_{CCD,i}$ [volts/px$^2$]:

$$E_{R,i} = \frac{V_{CCD,i}E_{DNI}}{\rho_{R,i}\tan^2(\frac{\gamma}{2})} \frac{\pi r^2_{sun\_pixels}}{\sum_{sun} V_{CCD\_sun,i}}, \quad (9)$$

where the term $$\frac{\sum_{sun} V_{CCD\_sun,i}}{\pi r^2_{sun\_pixels}}$$

is equivalent to the average pixel value in the Sun image. For the same camera and settings, this value can be calculated a single time and used for subsequent calculations of the irradiance at the central receiver 204. As indicated above, the reflectivity across the surface of the central receiver 204 can be determined in a variety of manners, and several exemplary manners for estimating/computing reflectivity are provided below.

The average reflectivity of the surface of the central receiver 204, $\rho_R$, can be determined by calibrating the reflectivity to yield a known integrated power irradiated on the central receiver 204 from a concentrator (heliostat or facet), assuming that no spillage occurs from the central receiver 204. This ensures conservation of energy in the predicted irradiance distribution and the method for computing reflectivity can be carried out as described below.

First, a measurement or estimate of reflectivity of a heliostat or facet, $\rho_h$, that will be used to illuminate the central receiver 204 can be determined. Thereafter, a camera can be utilized to capture an image of the heliostat or facet beam on the central receiver 204. The entirety of the beam should be visible in the resulting photograph without spillage. As mentioned above, appropriate filters can be utilized to prevent saturation of the CCD. Thereafter, a photograph of the central receiver 204 can be generated without the beam through utilization of the same camera and camera settings (zoom, f-stop, shutter speed, etc.) as was used when capturing the photograph of the beam on the central receiver 204. Additionally, an image of the Sun 106 can be captured utilizing the same camera and camera settings (or a different camera with the same camera settings). Finally, the average reflectivity of the central receiver 204 can be computed using the equation derived below (accounting for attenuation factors of the filters in the resultant pixel values).

Conversion of energy requires that if no spillage occurs, the power on the central receiver 204 $P_R$ [W] is equal to the power reflected from the heliostat $P_H$ [W].

$$P_R = P_H. \quad (10)$$

Figure 6:
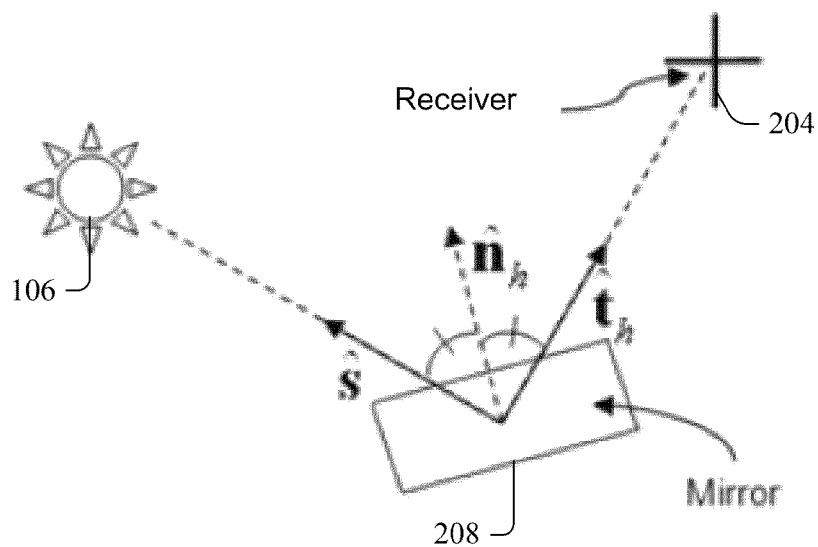
FIG. 6 illustrates a vectors utilized to determine parameters that can be employed in connection with computing reflectivity across a surface of a central receiver on a solar power tower.

Eq. 10 neglects atmospheric attenuation of the beam between the heliostat and the central receiver 204. Eq. 10 can be modified to consider atmospheric attenuation by subtracting the power lost due to atmospheric attenuation from the right-hand-side of Eq. 10. This change would be carried through subsequent equations that use Eq. 10. The power reflected by the concentrator (heliostat) can be given by the following:

$$P_h = E_{DNI}A_h\rho_h(\hat{s}\cdot\hat{n}_h) \quad (11)$$

where $A_h$ is the reflective area of the concentrator [m²], $\rho_h$ is the reflectivity of the concentrator, $\hat{s}$ is the unit Sun vector, and the unit normal $\hat{n}_h$ of the concentrator bisects $\hat{s}$ and the specular reflected vector $\hat{t}_h$ as shown in FIG. 6.

The total power irradiated on the central receiver 204 due to the heliostat beam can be given by the following equation:

$$P_R = \Sigma_{beam} E_{R,i} A_{R,i}, \quad (12)$$

where $E_{R,i}$ [W/m²] is the irradiance incident on a surface element area of the central receiver 204, $A_{R,i}$ [m²], that is imaged by pixel i. The surface element area of the central receiver, $A_{R,i}$, is given in Eq. (7). Eq. (9), which calculates $E_{R,i}$, is modified slightly to account for the ambient lighting, which may contribute to a non-negligible amount of irradiance received on the central receiver 204 from only a single heliostat or facet (as opposed to a much larger irradiance from an entire heliostat field):

$$E_{R,i} = \frac{(V_{CCD,i} - V_{CCD,i\_ambient})E_{DNI}}{\rho_{R,i}\tan^2(\frac{\gamma}{2})} \frac{\pi r^2_{sun\_pixels}}{\sum_{sun} V_{CCD\_sun,i}}, \quad (13)$$

where $V_{CCD,i}$ is the CCD pixel value in a single pixel on the photograph of the central receiver 204 with the beam, and $V_{CCD,i\_ambient}$ is the CCD pixel value at the same pixel on the photograph of the central receiver 204 without the beam (only ambient lighting). Combining Eqs. (11)-(13) in Eq. (10), and assuming r and θ are approximately the same for all points in the central receiver 204, yields the average reflectivity for the central receiver 204 as follows:

$$\rho_R = \frac{\pi r^2}{A_h\rho_h(\hat{s}\cdot\hat{n}_h)\cos(\theta)} \frac{\sum_{beam}(V_{CCD,i} - V_{CCD,i\_ambient})}{\sum_{sun} V_{CCD\_sun,i}} \quad (14)$$

This produces an effective reflectivity $\rho_R$ for an entire surface of the central receiver 204 illuminated by a collector beam. If the reflectivity distribution on the central receiver 204 is highly variable, than a reflectivity distribution $\rho_{R,i}$ can be determined to accurately calculate the incident irradiance on each surface element of the central receiver 204, $A_{R,i}$, using Eq. (9). Pursuant to an example, this can be done by imaging a coupon of known reflectivity in the field of view of the image of the central receiver 204. Assuming the lighting conditions on the coupon and central receiver 204 are substantially similar, the pixel values and reflectivity of the coupon can be used to scale the pixel values of the central receiver 204 and calculate the receiver reflectivity distribution $\rho_{R,i}$ as follows:

$$\rho_{R,i} = \rho_C \frac{V_{CCD,i}}{\overline{V}_{CCD,C}}, \quad (15)$$

where $\rho_C$ is the coupon reflectivity, $V_{CCD,i}$ is the pixel value corresponding to the central receiver 204 element imaged by pixel i, and $\overline{V}_{CCD,C}$ is the average pixel value of the coupon image.

Above, computation of reflectivity distribution of a receiver has generally been described. Oftentimes, a receiver may have a tubular surface, and accordingly it is desirable to compute reflectivity across the tubular surface of the receiver. To compute such reflectivity of the tubular surface, reflectivity of a heliostat or facet, $\rho_h$, can be estimated or measured. Thereafter, an image of the heliostat or facet beam on the receiver can be captured, where the entirety of the beam is visible in the image (without spillage). An image of the receiver can then be captured without the beam, using the same camera settings as were used when capturing the image of the heliostat or facet beam on the receiver. An image of the Sun can be captured or retrieved, again with the same camera settings. The reflectivity of the tube across the surface can be computed based at least in part upon the captured images.

When capturing an image of the tubular receiver with the camera, positioning of the camera can be taken into consideration. Specifically, the camera is desirably a distance from the tubular receiver such that the entire hemi-cylindrical receiving surface of each tube is visible to the camera. If the camera is too close, the tubes may block regions of neighboring tubes from view, which can result in inaccuracies in an average reflectivity calculation. Similar inaccuracies may result from an incorrect viewing angle; if the camera views the tubular receiver at an angle, then the plane containing the line of sight and the receiver normal should be parallel to the receiver tubes. Otherwise, the tubes may block regions of neighboring tubes from view. The derivation described below assumes an acceptable camera position. Additionally, if a cylindrical tube receiver comprises multiple flat panels facing different directions, then a photograph of each panel can be obtained with the camera position adjusted for each panel.

Eqs. (10), (11), and (12) can be utilized to model a total power irradiated on the tubular receiver due to a heliostat beam on such receiver. The receiver surface element area, $A_{R,i}$, for a tubular receiver can be given by the following algorithm:

$$A_{R,i} = L_{R,i}^{\perp} L_{R,i}^{\parallel} \tag{16}$$

where $$L_{R,i}^{\perp}$$

and $$L_{R,i}^{\parallel}$$

are lengths along the surface of a tube corresponding to the sides of pixel i in an image of the tube.

$$L_{R,i}^{\perp}$$

corresponds to the side of the pixel that is perpendicular to the length of the tube, while $$L_{R,i}^{\parallel}$$

corresponds to the side of the pixel that is parallel to the length of the tube.

Figure 7:
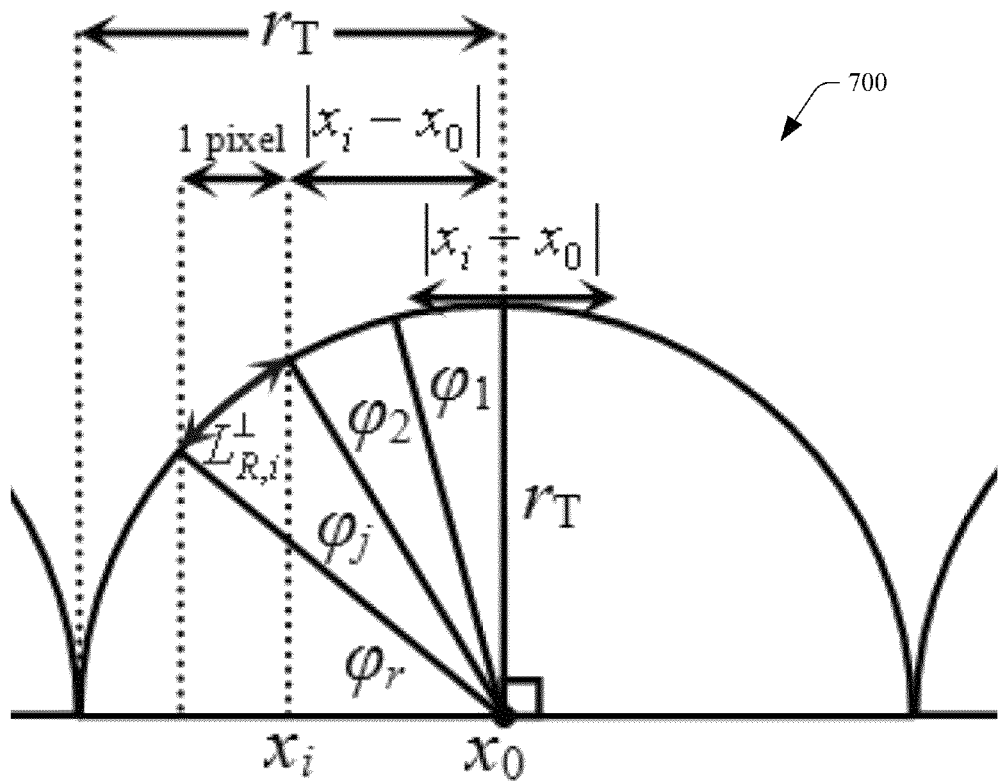
FIG. 7 illustrates an exemplary depiction of a portion of a tubular receiver.

Referring briefly to FIG. 7, an exemplary diagram of a tubular receiver 700 is illustrated. In FIG. 7, $$L_{R,i}^{\perp}$$

is shown as the arc-length on the receiver tube that corresponds to a length of 1 px in the image. The edge of this pixel is shown as being located at position $x_i$. The radius of the tube, $r_T$, is centered at position $x_0$. As shown in FIG. 7, $$L_{R,i}^{\perp}$$

is given in terms of the tube radius, $r_T$, by the following algorithm:

$$L_{R,i}^{\perp} = r_T \varphi_j \tag{17}$$

Figure 8:
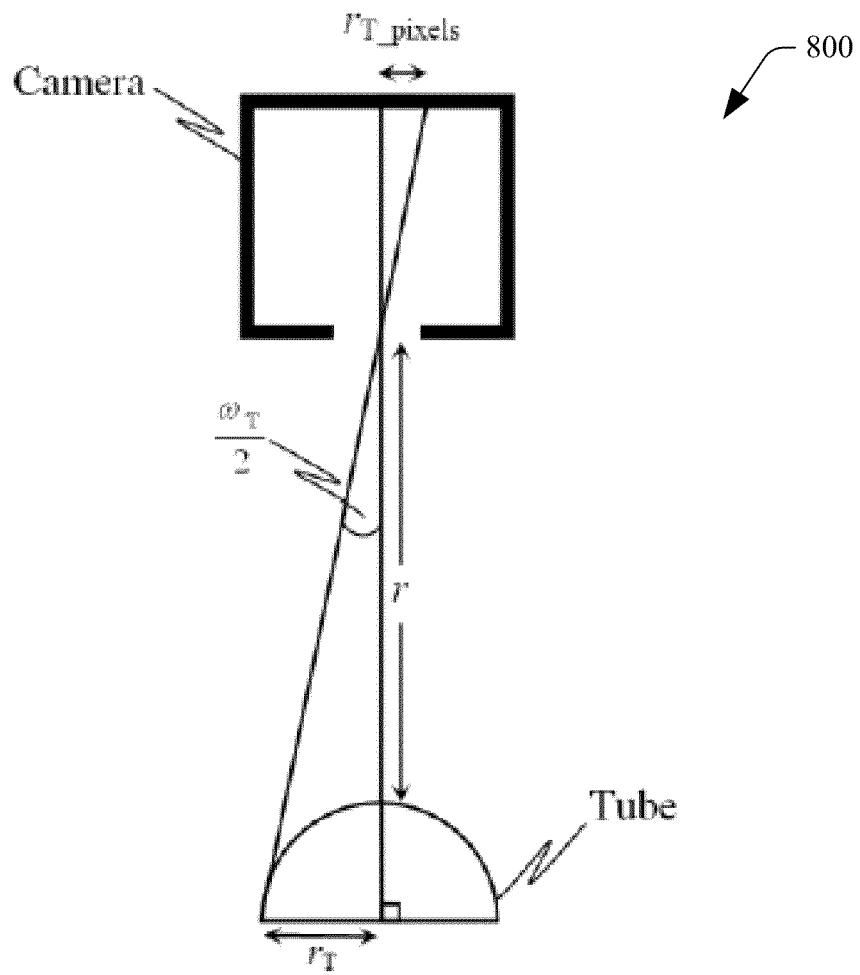
FIG. 8 illustrates a correlation between a radius of a tubular receiver in pixels and the actual radius of the tubular receiver.

The tube radius need not be known, and can be calculated from the image of the tubular receiver and the image of the Sun. With reference briefly to FIG. 8, an exemplary diagram 800 illustrating a correlation between the radius of the tube in pixels and the distance between the camera and the tubular receiver is illustrated. From FIG. 8, the following can be ascertained:

$$r_T = r\tan\left(\frac{\omega_T}{2}\right), \tag{18}$$

where r is the distance from the camera to the tube and $\omega_T$ is the angle subtended at the camera by the tube.

Figure 9:
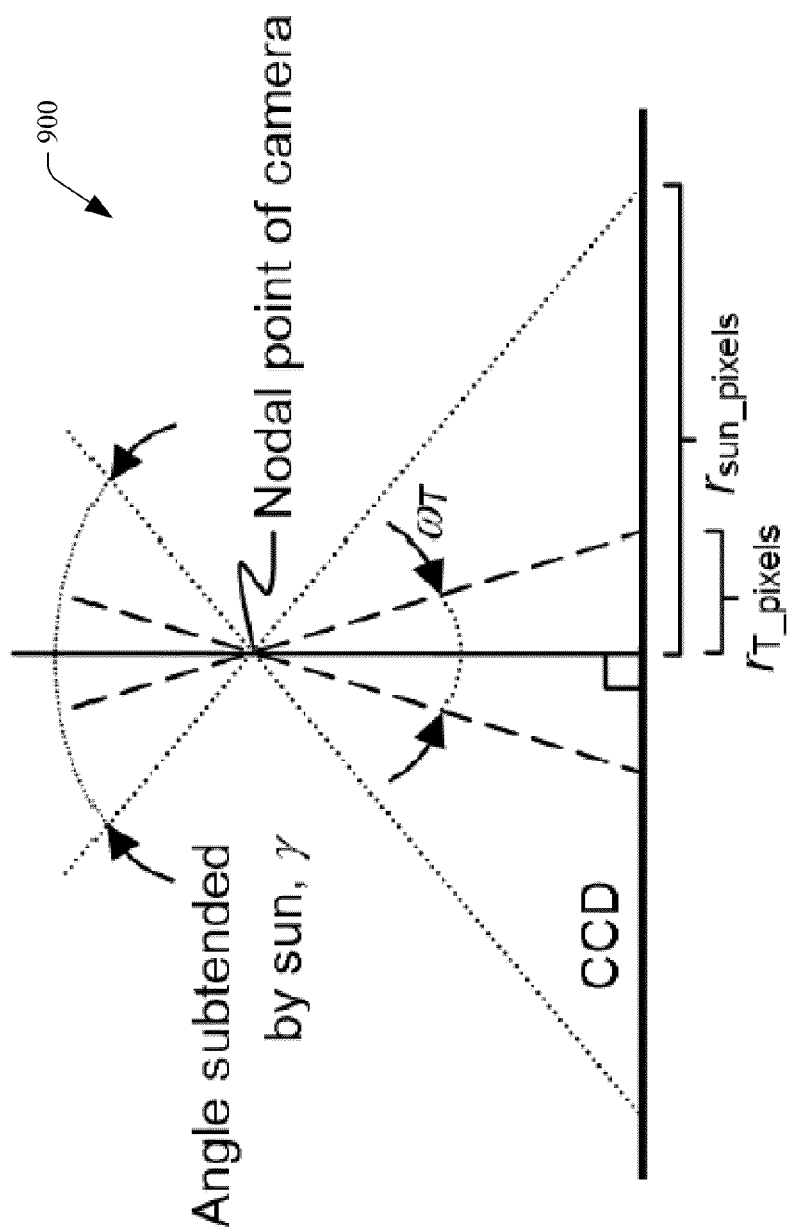
FIG. 9 is an exemplary illustration of pixels in a CCD camera.

Now turning to FIG. 9, a diagram 900 that illustrates determination of $\omega_T$ by comparing angles projected onto a CCD (for example) using the sun half-angle ($\gamma/2$) as a scaling factor is shown. From FIG. 9, the following can be obtained:

$$\frac{\tan\omega_T/2}{r_{T\_pixels}} = \frac{\tan\gamma/2}{r_{sun\_pixels}}, \tag{19}$$

where $r_{sun\_pixels}$ is the number of CCD pixels along the radius of the sun image, and $\gamma$ is the angle subtended by the sun. Therefore, Eqs. (18) and (19) yield the radius of the tube:

$$r_T = r\tan\gamma/2 \frac{r_{T\_pixels}}{r_{sun\_pixels}} \tag{20}$$

Figure 10:
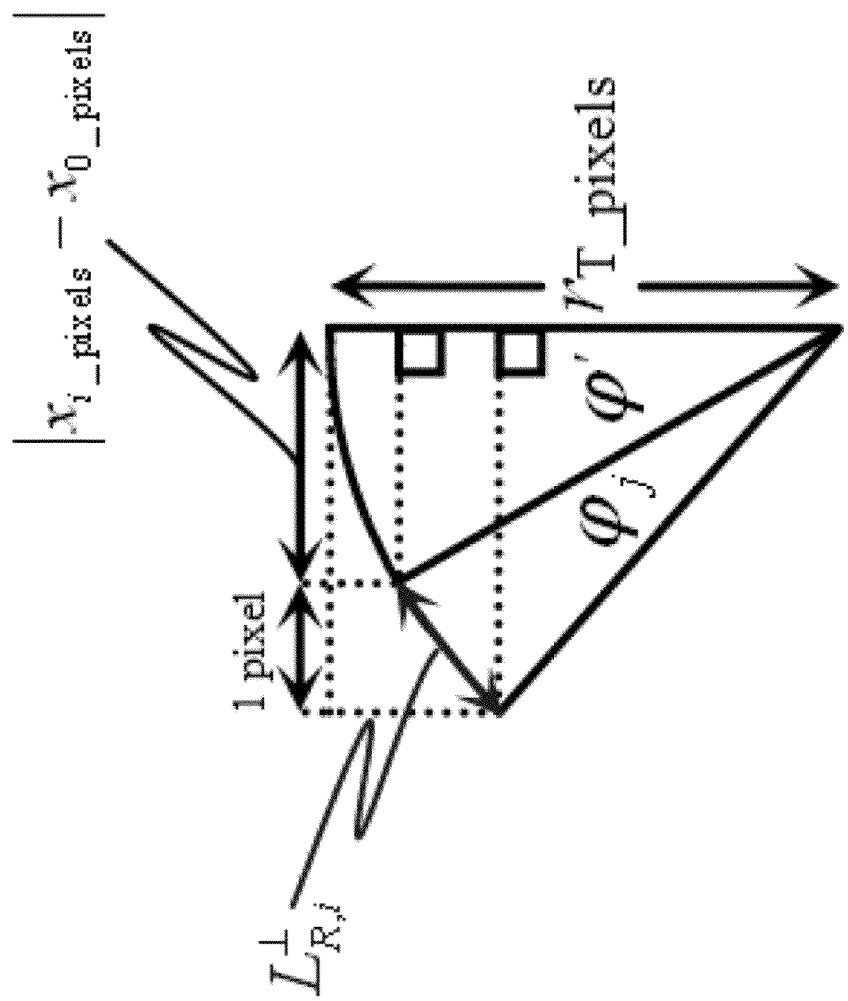
FIG. 10 is an exemplary illustration of a portion of a tubular receiver that can be utilized when computing the reflectivity of the tubular receiver.

In order to calculate $\phi_j$, the triangles in FIG. 10 can be constructed. The quantities $x_{i\_pixels}$, $x_{0\_pixels}$, and $r_{T\_pixels}$ are measured in pixels and are readily available from the photograph of the receiver. The triangles shown in FIG. 10 give the following algorithms:

$$\sin\varphi' = \frac{x_{i\_pixels} - x_{0\_pixels}}{r_{T\_pixels}} \tag{21}$$

$$\sin(\varphi_j + \varphi') = \frac{|x_{i\_pixels} - x_{0\_pixels}| + 1\,pixel}{r_{T\_pixels}} \tag{22}$$

Eqs. (21) and (22) yield the angle $\phi_j$ in terms of values available from the photograph:

$$\varphi_j = \arcsin\left(\frac{|x_{i\_pixels} - x_{0\_pixels}| + 1\, pixel}{r_{T\_pixels}}\right) - \left(\frac{|x_{i\_pixels} - x_{0\_pixels}|}{r_{T\_pixels}}\right) \quad (23)$$

Combining Eqs. (17), (20), and (23) yields the following equation for $$L_{R,i}^{\perp}:$$

$$L_{R,i}^{\perp} = r\tan\gamma/2 \frac{r_{T\_pixels}}{r_{sun\_pixels}} \left[\arcsin\left(\frac{|x_{i\_pixels} - x_{0\_pixels}| + 1\, pixel}{r_{T\_pixels}}\right) - \left(\frac{|x_{i\_pixels} - x_{0\_pixels}|}{r_{T\_pixels}}\right)\right] \quad (24)$$

Figure 14:
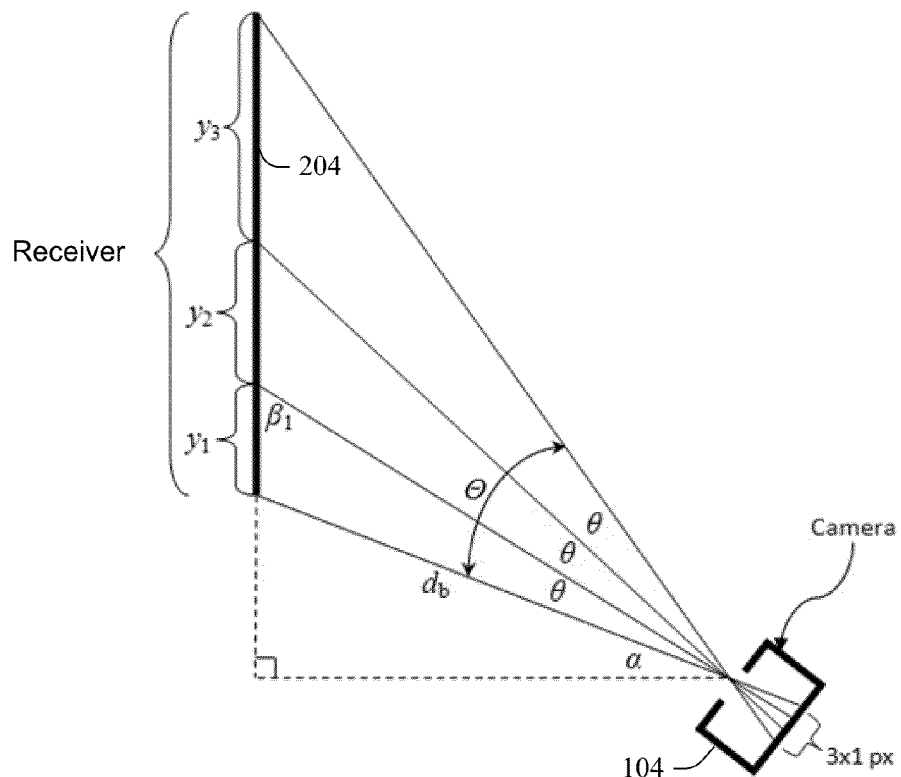
FIG. 14 illustrates a determination of length measurements on a receiver surface that correspond to pixels in an image of the receiver.

The length $$L_{R,i}^{\parallel}$$

can be obtained by a perspective unwrapping method that is described in detail below. Referring to FIG. 14, $$L_{R,i}^{\parallel}$$

is equal to the corresponding $\gamma_k$ value. Therefore, $$L_{R,i}^{\parallel}$$

can be obtained as follows:

$$L_{R,i}^{\parallel} = d_b\left[\frac{\sin k\theta}{\cos\alpha + k\theta} - \frac{\sin k\theta - \theta}{\cos\alpha + k\theta - \theta}\right], \quad (25)$$

where $d_b$ is the distance to the base of the receiver, the base point subtends an angle $\alpha$ above the horizontal at the camera shown in FIG. 14, and $\theta$ is given by the following:

$$\theta = \frac{2\arctan\left[\frac{Y_{receiver\_pixels}}{2r_{sun\_pixels}}\tan\gamma/2\right]}{Y_{receiver\_pixels}}, \quad (26)$$

where $Y_{receiver\_pixels}$ is the height of the receiver (the length of the tube) in pixels. It can further be noted that the integer k in Eq. (25) is subject to the following constraint:

$$1 \le k \le Y_{receiver\_pixels} \quad (27)$$

Eq. (13) illustrates a computation for $E_{R,i}$, where $V_{CCD,i}$ is the CCD pixel value at a single pixel on the image of the receiver with the beam and $V_{CCD,i\_ambient}$ is the CCD pixel value at the same pixel on the image of the receiver without the beam (only ambient lighting). If it is assumed that reflectivity is uniform for every point on the receiver, then $\rho_{R,i}$ can be substituted in Eq. (13) with the average reflectivity, $P_R$. Combining Eqs. (11), (12), and (16) into Eq. (10), and using the result in Eq. (13) can yield the average reflectivity for the receiver:

$$\rho_R = \frac{\pi r_{sun\_pixels}^2}{A_h \rho_h(\hat{s}\cdot\hat{n}_h)\tan^2(\gamma/2)} \frac{\Sigma_{beam} L_{R,i}^{\perp} L_{R,i}^{\parallel}(V_{CCD,i} - V_{CCD,i\_ambient})}{\Sigma_{sun} V_{CCD\_sun,i}} \quad (28)$$

The computing device 110 can compute the irradiance distribution across the surface of a tubular receiver based at least in part upon this average reflectivity of the surface of the receiver.

After the computing device 110 has computed the irradiance distribution received at the central receiver 204 corresponding to pixels in the image of the central receiver 204, it may be beneficial to measure a size in meters of a certain feature on the central receiver 204. For example, if the central receiver 204 is cylindrical, a user may benefit from knowing the angular position along the central receiver 204 circumference that corresponds to a certain irradiance point of interest that corresponds to a pixel in the image of the central receiver 204. The computing device 110 can be configured with instructions that convert pixel lengths on the horizontal and vertical axes of an irradiance map into spatial dimensions on the central receiver 204, measured in meters or degrees.

In general, the meters per pixel conversion factor is not constant, as it can be affected by the perspective of the camera that was utilized to capture the image of the central receiver 204. For instance, if a photographer who was standing on the ground obtained a photograph of the central receiver 204 mounted on top of the tower 202, the conversion of vertical pixels to meters along the height of the central receiver 204 must consider that the meters per pixel conversion factor for a pixel at the top of the image will be larger than at the bottom of the image. Similarly, for the conversion of horizontal pixel lengths to meters along the width of a flat-panel central receiver 204, the meters per pixel for a point closer to the camera will be smaller than for a point further from the camera. If the central receiver 204 is cylindrical, the center of the image will correspond to a smaller subtended angle per pixel than at the edge of the image.

Figure 11:
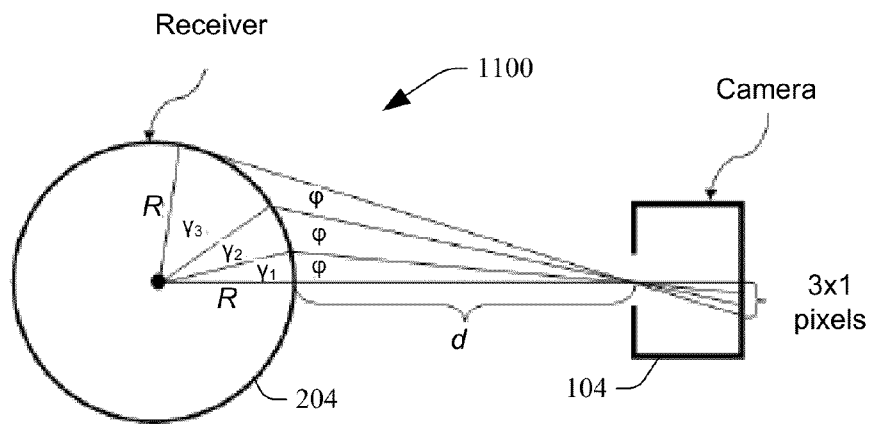
FIG. 11 illustrates a mapping of pixels to spatial portions of a cylindrical solar receiver at a solar power tower.
Figure 12:
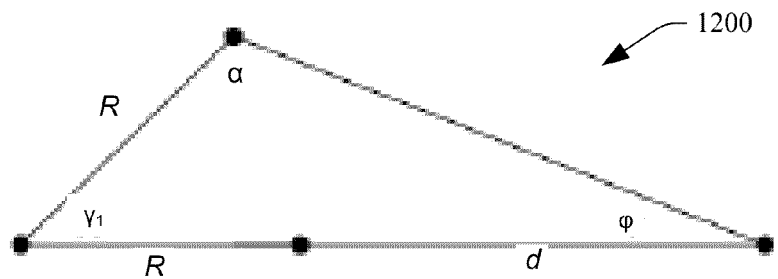
FIG. 12 is a geometric diagram that illustrates an angle that is subtended by the center of a central receiver on its surface.

Turning now to FIG. 11, a diagram 1100 that illustrates computation of subtended angle per pixel when the central receiver 204 is in the form of a cylinder is illustrated. Here, the camera 104 is positioned to capture an image of the central receiver 204, which is cylindrical in shape. The camera 104 is a distance d from a cylindrical receiver of radius R. It can be noted that d and R need not be known when capturing the image of the central receiver 204. One pixel in the CCD of the camera 104 corresponds to an angle $\phi$ of incoming light. It may be desirable to determine the angles subtended by the center of the central receiver 204 on its surface ($\gamma_1, \gamma_2, \ldots$). Referring briefly to FIG. 12, a triangle 1200 that illustrates the angles subtended by the center of the central receiver 204 on its surface is illustrated.

From the Law of Sines, the following can be obtained:

$$\frac{\sin(\alpha)}{R+d} = \frac{\sin(\varphi)}{R} \Rightarrow \alpha = \pi - \arcsin\left[\left(1 + \frac{d}{R}\right)\sin(\varphi)\right]. \quad (29)$$

The arcsin is subtracted from $\pi$ because $\alpha$ is necessarily obtuse. Eq. (29) provides the following:

$$\gamma_1 = \pi - (\alpha + \phi) = \arcsin[(1+d/R)\sin(\phi)] - \phi. \quad (30)$$

The sum $(\gamma_1+\gamma_2)$ can be obtained by replacing $\phi$ with $2\phi$ in Eq. (30):

$$\gamma_1+\gamma_2=\arcsin[(1+d/R)\sin(\phi)]-2\phi. \quad (31)$$

Similarly for some positive integer k, the following can be obtained:

$$\sum_{i=1}^{k}\gamma_i = \arcsin\left[\left(1+\frac{d}{R}\right)\sin(k\varphi)\right]-k\varphi \Rightarrow \gamma_k = $$
$$\arcsin\left[\left(1+\frac{d}{R}\right)\sin(k\varphi)\right]-k\varphi-\sum_{i=1}^{k-1}\gamma_i = \arcsin\left[\left(1+\frac{d}{R}\right)\sin(k\varphi)\right]-$$
$$k\varphi - \left\{\arcsin\left[\left(1+\frac{d}{R}\right)\sin(k\varphi-\varphi)\right]-(k-1)\varphi\right\} \quad (32)$$

Therefore an arbitrary $\gamma_k$ can be given by the following:

$$\gamma_k = \arcsin\left[\left(1+\frac{d}{R}\right)\sin(k\varphi)\right]-\arcsin\left[\left(1+\frac{d}{R}\right)\sin(k\varphi-\varphi)\right]-\varphi. \quad (33)$$

As mentioned above, it is not necessary to know R and d in order to calculate each $\gamma_k$. Instead, the user can draw a horizontal line in the image of the central receiver 204 that indicates the total visible width of the central receiver 204. Alternatively, this can be done through utilization of an image processing system.

Figure 13:
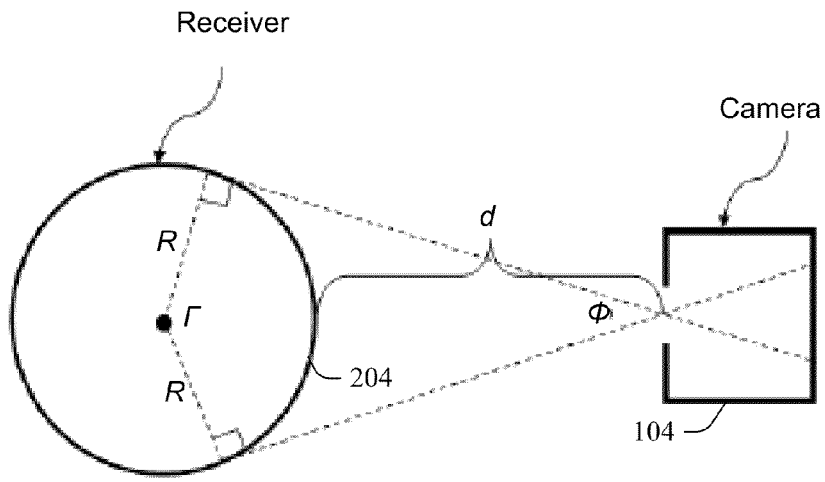
FIG. 13 is a geometric diagram that illustrates the relationship between camera to receiver distance, cylindrical receiver radius, and various subtended angles.

In the diagram shown in FIG. 13, $\Phi$ is the total angle subtended at the camera 104 by the visible portion of the central receiver 204. $\Gamma$ is the total angle subtended by the visible portion of the central receiver 204 at its center. Accordingly, the following can be obtained:

$$\Phi = 2\arcsin\left(\frac{R}{R+d}\right) \Rightarrow \frac{d}{R} = \frac{1}{\sin(\Phi/2)}-1. \quad (34)$$

Placing Eq. (34) into Eq. (32) can yield an equation for $\gamma_k$ without R or d:

$$\gamma_k = \arcsin\left[\frac{\sin(k\varphi)}{\sin(\Phi/2)}\right] - \arcsin\left[\frac{\sin(k\varphi-\varphi)}{\sin(\Phi/2)}\right] - \varphi \quad (35)$$

Utilizing the image of the Sun 106 and the image of the central receiver 204 to determine the radius of the Sun in pixels, $r_{sun}(px)$, and radius of the central receiver 204 in pixels, $r_{receiver}(px)$, an equation for $\Phi$ can be obtained:

$$\Phi = 2\arctan\left[\frac{r_{receiver}(px)}{r_{sun}(px)}\tan\left(\frac{\gamma}{2}mrad\right)\right]. \quad (36)$$

$\varphi$ can be obtained by noting that $\Phi$ is the sum of all $\varphi$:

$$\Phi = 2\cdot\varphi\cdot r_{receiver}(px) \Rightarrow \varphi = \frac{\Phi}{2\cdot r_{receiver}(px)}. \quad (37)$$

Eqs. (36) and (37) yield a solution for each $\gamma_k$ in terms of $r_{sun}(px)$ and $r_{receiver}(px)$ only. It can be noted that the integer k in Eq. (34) may be subject to the following constraint:

$$1\leq k\leq r_{receiver}(px). \quad (38)$$

With reference now to FIG. 14, a perspective of the camera 104 with respect to the central receiver 204 for conversion of pixel height to corresponding spatial height on the central receiver 204 is illustrated. It is to be understood that similar techniques can be utilized to convert pixel width to spatial width on the central receiver 204 if the central receiver 204 is planar. In the example shown in FIG. 14, the camera 104 is a distance $d_b$ from the base of a vertical face of the central receiver 204, and this base point subtends an angle $\alpha$ above the horizontal at the camera 104. Both $d_b$ and $\alpha$ can be measured using a range finder, for instance. One pixel on the camera 104 corresponds to an angle $\theta$ of incoming light. The entire height of the central receiver 204 subtends an angle $\Theta$ at the camera 104. It is thus desirable to determine the receiver height $(y_1, y_2, \ldots)$ that corresponds to each resultant pixel in the image of the central receiver 204. The angle $\beta_1$ can be given by the following:

$$\beta_1 = \frac{\pi}{2}-(\alpha+\theta). \quad (39)$$

From the Law of Sines, the following can be obtained:

$$\frac{y_1}{\sin(\theta)} = \frac{d_b}{\sin\beta_1} \Rightarrow y_1 = d_b\frac{\sin(\theta)}{\sin\left[\frac{\pi}{2}(\alpha+\theta)\right]} \Rightarrow d_b\frac{\sin(\theta)}{\cos(\alpha+\theta)}. \quad (40)$$

The sum $(\gamma_1+\gamma_2)$ can be obtained by replacing $\theta$ in Eq. (39) with (20):

$$y_1+y_2 = d_b\frac{\sin(2\theta)}{\cos(\alpha+2\theta)}. \quad (41)$$

Similarly, for some positive integer k, the following can be obtained:

$$\sum_{i=1}^{k}y_i = d_b\frac{\sin(k\theta)}{\cos(\alpha+k\theta)} \Rightarrow d_b\frac{\sin(k\theta)}{\cos(\alpha+k\theta)}-\sum_{i=1}^{k-1}y_i. \quad (42)$$

Therefore, an arbitrary $\gamma_k$ can be given by the following:

$$y_k = d_b\left[\frac{\sin(k\theta)}{\cos(\alpha+k\theta)}-\frac{\sin(k\theta-\theta)}{\cos(\alpha+k\theta-\theta)}\right]. \quad (43)$$

Using the image of the Sun 106 and the image of the central receiver 204 to determine the diameter of the Sun, $d_{sun}(px)$, in pixels and height of the central receiver 204, $Y_{receiver}(px)$, in pixels, respectively, an equation for $\Theta$ can be as follows:

$$\Theta = 2\arctan\left[\frac{y_{receiver}(px)}{d_{sun}(px)}\right]\tan\left(\frac{\gamma}{2}mrad\right). \quad (44)$$

$\theta$ can be obtained by noting that $\Theta$ is the sum of all $\theta$:

$$\theta = \frac{\Theta}{Y_{receiver}(px)}. \quad (45)$$

It is to be noted that integer k in equation (43) is subject to the following constraint:

$$1 \leq k \leq Y_{receiver}(px). \quad (46)$$

Figure 15:
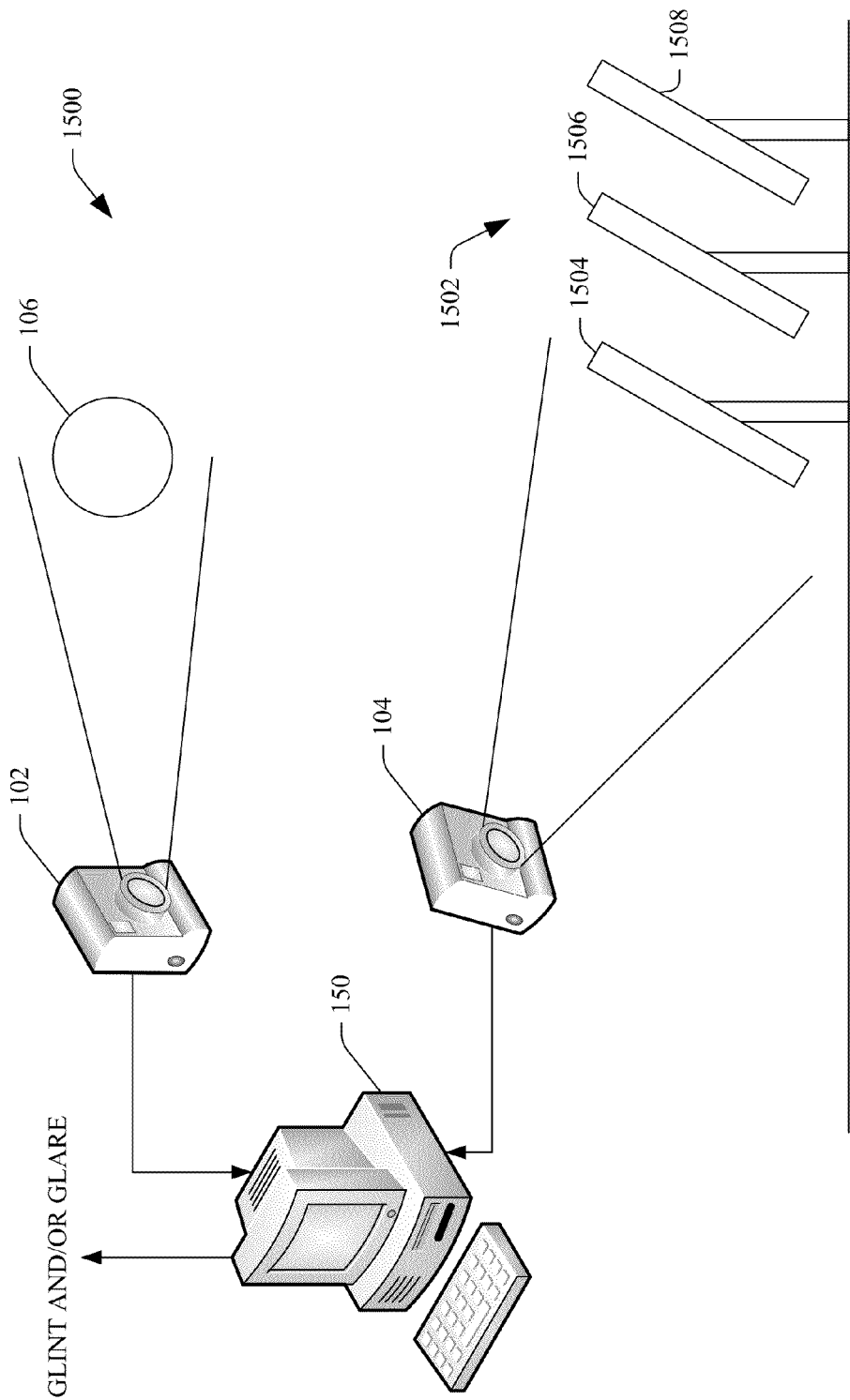
FIG. 15 is a system that facilitates computing a measure of glint and/or glare emitted from a reflective source through utilization of an image of the Sun and an image of the reflective source.

Now referring to FIG. 15, an exemplary system 1500 that facilitates computing glint/glare emitted from a reflective entity is illustrated. The system 1500 comprises a concentrator field 1502 that includes a plurality of concentrators 1504-1508. These concentrators 1504-1508 maybe heliostats, facets, reflective troughs or other suitable reflective entities. Furthermore, rather than being a reflective concentrator, the entity may be a receiver.

The system 1500 additionally comprises the first digital camera 102 that captures an electronic image of the Sun 106 and the second digital camera 104 that is configured to capture an electronic image of the reflective entity. The computing device 110 is in communication with the first digital camera 102 and the second digital camera 104 and receives the electronic image of the Sun 106 generated by the first digital camera 102 and the electronic image of the reflective entity (one or more concentrators in the concentrator field 1502) captured by the second digital camera 104. The computing device 110 includes computer-executable instructions for computing glint and/or glare based at least in part upon values of pixels in the electronic image of the Sun 106 and values of pixels in the electronic image of the reflective entity. The glint and/or glare computed by the computing device 110 may then be output to a user. In a particular embodiment, a single mobile computing device such as a mobile telephone can be utilized to capture an image of the Sun 106 (or receive a previous image of the Sun 106) and capture an image of the reflective entity. The portable computing device may then be configured to compute the glint and/or glare based at least in part upon the pixel values of the image of the Sun 106 and the pixel values of the image of the concentrators 1502.

The computed glint and/or glare at computing device 110 can be mapped to one or more ocular safety metrics. For instance, an ocular safety metric may identify an amount of solar radiation received at the human eye at a particular subtended source angle that can cause permanent eye damage (retinal burn), potential for temporary after image (flash blindness), and low potential for temporary after image. If the irradiance received by the human eye is sufficiently large for a given subtended source angle, permanent eye damage from retinal burn may occur. It can be noted that as the subtended source angle increases, a safe retinal irradiance threshold decreases due to the increased size of the retinal image area and hence the increased energy applied to the retina area. Various ocular safety metrics have been presented, and all of such metrics and are contemplated for utilization in connection with the system 1500.

Models for computing retinal irradiance for various types of reflective entities will now be described. Retinal irradiance [W/m²] can be calculated from a total amount of power entering the pupil of the human eye and the retinal image area. The diameter $d_r$ of the image projected onto the retina (assuming circular images) can be determined from the source angle ($\omega$), which can be calculated from the source size ($d_s$), radial distance (r) between the eye and the source, and the focal length of the eye (f≅0.017 m) as follows:

$$d_r = f\omega, \quad (47)$$

where $\omega = d_s/r$.

Eq. (47) assumes that the arc and the chord of a circle are the same for small angles. At a source angle, $\omega$, of 60°, the error in $d_r$ may be approximately 5%. If the irradiance at a plane in front of the cornea, $E_C$(W/m²) is known, the power entering the pupil can be calculated as the product of the irradiance and the pupil area (the diameter of the pupil, $d_p$, adjusted to Sunlight is approximately 2 mm). The power can then be divided by the retinal image area and multiplied by a transmission coefficient, $\tau(\sim 0.5)$, for the ocular media (to account for absorption of radiation within the eye before it reaches the retina) to yield the following expression for the retinal irradiance:

$$E_r = E_c \left(\frac{d_p^2}{d_r^2}\right) \tau. \quad (48)$$

Now described are analytical methods for calculating the irradiance caused by specular and diffuse reflection of solar radiation as a function of distance and other characteristics of the source. Specular reflections occur from polished mirror-like surfaces so that the reflective angle is equal to the incident angle relative to the surface normal. Diffuse reflections occur from uneven or rough surfaces that scatter the incident radiation such that the radiance is uniform in all directions. Described first will be an analytical model corresponding to specular reflections. Direct specular solar reflection from mirrors can cause glint and glare hazards when heliostats, for instance, are in standby positions reflecting Sun at locations other than the receiver. Specular solar reflections from heliostats, dishes and parabolic troughs can cause glint and glare hazards when the collectors are in off-axis positions (e.g., when moving from a stowed position to a tracking position). For parabolic troughs, glint and glare from specular reflections can also occur when the Sun is low in the horizon and align with the axis of the trough causing reflected rays to spill from the end of the trough.

Figure 16:
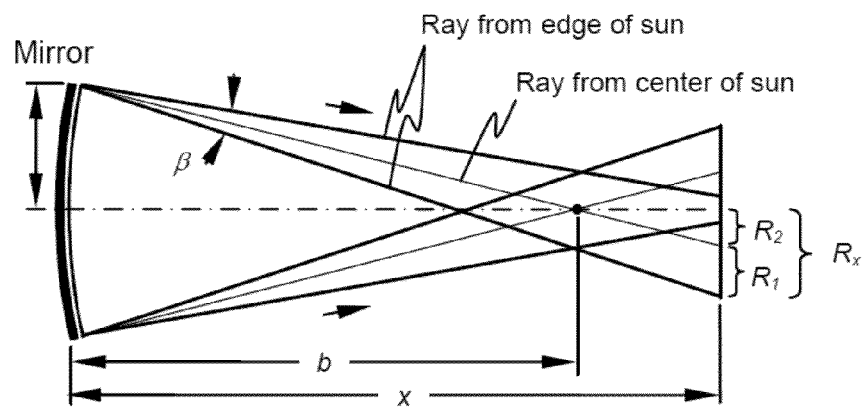
FIG. 16 is a diagram that illustrates the geometry of specular solar reflections from a focused mirror.

With reference to FIG. 16, geometry of specular solar reflections from a focused mirror is illustrated. An analytical model of beam irradiance resulting from specular solar reflections from a point-focus mirror can be derived with the following assumptions: (1) uniform Sun intensity; (2) round, focused, continuous surface mirrors; (3), no cosine losses, off-axis aberrations or atmospheric attenuation; and (4), uniform intensity in beam cross section.

These assumptions will generally produce the largest beam irradiance, but the assumption of uniform Sun intensity averages the intensity over the entire beam. Using a non-uniform solar intensity creates larger peak fluxes towards the center of the beam. Comparisons with a ray tracing model shows that the difference in peak fluxes about 25 to 30% at the focal length, but the difference can be greater at other distances.

The beam irradiance I [W/cm²] may be calculated as the product of the direct normal irradiance, Q [W/cm²], the mirror reflectivity ρ, and the area concentration ratio, C, as follows:

$$I = \rho Q C \quad (49)$$

The direct normal irradiance, Q, at the Earth's surface is approximately 0.1 W/cm². The area concentration ratio C can be calculated as follows, assuming a circular mirror area, $A_h$, with radius, $R_h$, and a circular beam area, $A_x$, with radius, $R_x$, at a distance x from the mirror:

$$C = \frac{A_h}{A_x} = \left(\frac{R_h}{R_x}\right)^2. \quad (50)$$

The radius, $R_x$, of the beam is comprised of two components:

$$R_x = R_1 + R_2, \quad (51)$$

where $R_1$ is caused by the Sun angle and mirror contour inaccuracies (slope error) and $R_2$ represents focusing and defocusing characteristics of the beam at a distance that is less than or greater than the focal length. The beam divergence, $R_1$, at a distance x from the mirror is defined by the Sun half angle (approximately 4.7 mrad) and any additional slope errors caused by mirror inaccuracies:

$$R_1 \approx x \tan\left(\frac{\beta}{2}\right), \quad (52)$$

where $\beta/2$ is the half angle of the total beam divergence. This approximation may have an error that is less than 0.3% for $b/R_h > 18$, where b is the focal length. $R_2$ can be defined using similar triangles as shown in FIG. 12:

$$\frac{R_2}{|x-b|} = \frac{R_h}{b} \Rightarrow R_2 = \left|\frac{x}{b} - 1\right| R_h. \quad (53)$$

Using Eqs. (50), (51), (52), and (53) in equation (49) and the approximation that tan $$\left(\frac{\beta}{2}\right) = \frac{\beta}{2}$$

when $$\frac{\beta}{2}$$

is small, yields the following expression for the beam irradiance [W/cm²]:

$$I = \rho Q \left(\frac{x\beta}{D_h} + \left|\frac{x}{b} - 1\right|\right)^{-2} \text{ (point-focus collector)} \quad (54)$$

where $D_h = 2R_h$. The beam irradiance can also be presented in units of "Suns" by dividing Eq. (41) by Q ~0.1 W/cm²). The maximum beam irradiance occurs at the focal length x=b. In addition, the beam irradiance from a flat mirror can be calculated by setting b=∞ in Eq. (41). $D_h$ is the effective diameter of the mirror, which can be calculated from a total mirrored area of individual heliostats:

$$D_h = \left(\frac{4A_h}{\pi}\right)^{0.5}. \quad (55)$$

As defined in Eq. (49), the irradiance is proportional to the concentration ratio, which is equal to the ratio of the measured irradiance at a given distance to the product of the direct normal irradiance, Q, and the mirror reflectivity. The concentration ratio is also equal to the area ratio of the mirror and the beam size. It follows that the relative spot size of the reflected image of the Sun and the mirror at a given distance is proportional to the measured irradiance at that location. Once the irradiance, I, is determined, the spot size of the reflected image of the Sun and the mirror can be estimated by the following equation assuming that the spot size is proportional to the irradiance:

$$\frac{A_{spot}}{A_o} = \left(\frac{d_{spot}}{d_o}\right)^2 = \left(\frac{x\omega_{spot}}{x\beta}\right)^2 = C = \frac{I}{\rho Q} \Rightarrow \omega_{spot} = \beta \sqrt{\frac{I}{\rho Q}} \quad (56)$$

where A is the area of the reflected image on the mirror as viewed by an observer at a distance, x, away from the mirror; d is the diameter of the reflected image on the mirror; co is the subtended angle of the reflected Sun image on the mirror (Sun angle plus slope error) as observed from a prescribed distance; β is a beam divergence angle (Sun angle plus slope error); the subscript "spot" refers to the observed spot image on the mirror, and the subscript "o" refers to a nominal spot image of the Sun at an irradiance of one Sun times the mirror reflectivity (ρQ), i.e., the spot size observed on a large flat mirror ($b \to \infty$, $D_h \to \infty$). Thus if the measure of irradiance I is greater or less than ρQ, the observed size and subtended angle, $\omega_{spot}$, of the reflected spot image of the Sun will be greater or less than the nominal size and subtended angle, β, of the Sun image at a location x.

Using Eq. (56) in Eqs. (47) and (48) yields the following expression for the retinal irradiance, where a corneal irradiance, $E_C$, is set equal to irradiance I used in Eqs. (54) and (56):

$$E_r = \frac{\rho Q d_p^2 \tau}{f^2 \beta^2}. \quad (57)$$

It can be noted that the retinal irradiance in Eq. (57) does not depend on distance from the source (assuming no atmospheric attenuation). As distance increases, both the power entering the pupil and the retinal image are (which is proportional to the square of the subtended source angle) decrease at the same rate. Therefore, the retinal irradiance, which is equal to the power entering the pupil divided by the retinal image area, is independent of distance. The corneal irradiance, however, changes as a function of distance as given by Eq. (54).

The equations derived above with respect to determining the specular beam irradiance from point-focus collectors can be readily extended to line-focus (parabolic trough, linear Fresnel) collectors. The primary difference is that the concentration ratio in Eq. (50) is changed since the convergence/divergence of rays caused by the shape of the line focus mirror is primarily in one dimension (rather than two):

$$C = \frac{A_h}{A_x} = \frac{R_h}{R_x}. \quad (58)$$

The resulting irradiance from the specular reflections from a line focus collector then becomes:

$$I = \rho Q \left(\frac{x\beta}{D_h} + \left|\frac{x}{b} - 1\right|\right)^{-1} \text{ (line-focus collectors)} \quad (59)$$

Eq. (59) is similar in form to Eq. (54) for point-focus collectors. However, the irradiance from line-focus collectors decreases less rapidly with distance past the focal point. Eq.

(56) is still valid to describe the spot size of the reflected Sun image in the line-focus mirror. Using Eq. (56) and (59) in Eqs. (47) and (48) then yields the same expression for the retinal irradiance as Eq. (57) for point-focus collectors. The retinal irradiance is independent of distance, because the retinal image area decreases at the same rate as the irradiance, therefore the retinal irradiance can be constant.

Figure 17:
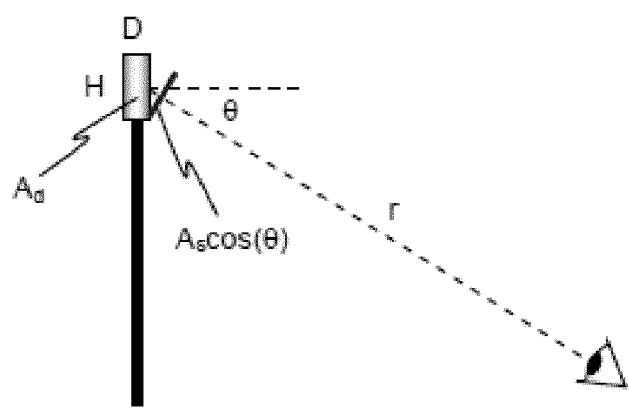
FIG. 17 illustrates parameters for diffuse reflection calculations corresponding to a cylindrical receiver.

An analytical model for diffuse reflections is now described. Reflections from receivers which are used to absorb the concentrated solar flux from heliostat, dish and trough collector systems can be modeled as diffuse rather than specular. Calculation of the irradiance at a location resulting from diffuse reflections depends on the total flux received by the reflecting source, reflectivity, size, and position of the source and distance to the source. First, the total power, $P_d$ emanating diffusely from the source is determined as follows:

$$P_d = (DNI)C(A_d)\rho \qquad (60)$$

where DNI is the direct normal irradiance, C is the concentration ratio (Eq. (50)), $A_d$ is the surface area of the diffuse source, and $\rho$ is the reflectivity of the diffuse source. For a diffuse source, it can be assumed that the reflected radiance is uniform in all directions, yielding the following equation for diffuse irradiance, $I_d$ (W/m²), as a function of radial distance, r (m):

$$I_d = \left(\frac{P_d}{\pi A_d}\right)\left(\frac{A_c \cos(\theta)}{r^2}\right), \qquad (61)$$

where the first term on the right-hand side of Eq. (61) is the diffuse reflected radiance [W/m²/sr], which is equal to the emissive flux $$\frac{P_d}{A_d}$$

divided by $\pi$. The radiance is multiplied by the solid angle subtended by the pupil of the eye. The radiance and solid angle are then multiplied by the ratio of the projected source area, $A_s \cos(\theta)$, and the pupil area to get the diffuse irradiance at the eye. The second term on the right-hand side of Eq. (61) is a product of the solid angle and the area ratio, where r is a radial distance of an observer relative to the source, $\theta$ is the angle between the surface normal and the line of sight between the source and the observer, and the pupil area cancels out. Note that as $\theta$ increases to 90°, the visible source area and the subtended solid angle go to zero. If the irradiating source is planar, then $A_d = A_s$. The potential for different areas of the diffuse source arise when a non-planar source exists, such as a cylindrical external central receiver. In this case, the diffuse source area, $A_d$, is equal to $\pi * D * H$, while the visible area, $A_s$, is approximately equal to $D*H$, where D is the diameter of the cylinder and H is the height. The projected area perpendicular to the line of sight is equal to $A_s \cos(\theta)$. Referring briefly to FIG. 17, a graphical representation of such parameters is illustrated.

Combining Eq. (61) with Eqs. (47) and (48) can yield the following expressions for the subtended angle, $\omega$[rad], and diffuse retinal irradiance, $E_{r,d}$ [W/m²], where the corneal irradiance, $E_C$, in Eq. (48) is set to equal the diffuse irradiance, $I_d$, and the source size, $d_s$, is determined using Eq. (55) with $A_h = A_s \cos(\Theta)$:

$$\omega = \sqrt{\frac{4A_s \cos(\theta)/\pi}{r}}. \qquad (62)$$

$$E_{r,d} = \frac{P_d d_p^2 \tau}{4A_d f^2}. \qquad (63)$$

Using the aforementioned models that illustrate that retinal irradiance can be computed, and glint/glare is a function of the retinal irradiance and the subtended source angle, the computing device 110 can compute the glint and/or glare emitted from a reflective entity as follows: the first digital camera 102 can capture an image of the Sun 106, wherein the amount of power emitted from the Sun is known (W/m²). Because the power emitted from the Sun is known, a conversion factor can be computed between power emitted from the Sun and pixel intensity values.

The second digital camera 104 can capture an image of the reflective entity, wherein such image comprises a plurality of pixels having a plurality of intensity values. An amount of solar radiation reflected from the reflective entity can be computed by scaling the intensity values of the reflective entity with the intensity values of the image of the Sun 106. Thus, solar irradiance reflected from the entity can be computed based at least in part upon the intensity values of the pixels in the image of the Sun 106 and the intensity values of pixels in the image of the reflective entity. This can be converted into ocular irradiance due to the known approximate size of the pupil of a human eye. As mentioned above, ocular safety depends on the subtended angle of the source, as well as the ocular irradiance received at the human eye. Accordingly, the subtended angle can be calculated and glint/glare can be computed to determine whether the reflective entity is a safety hazard.

Figure 18:
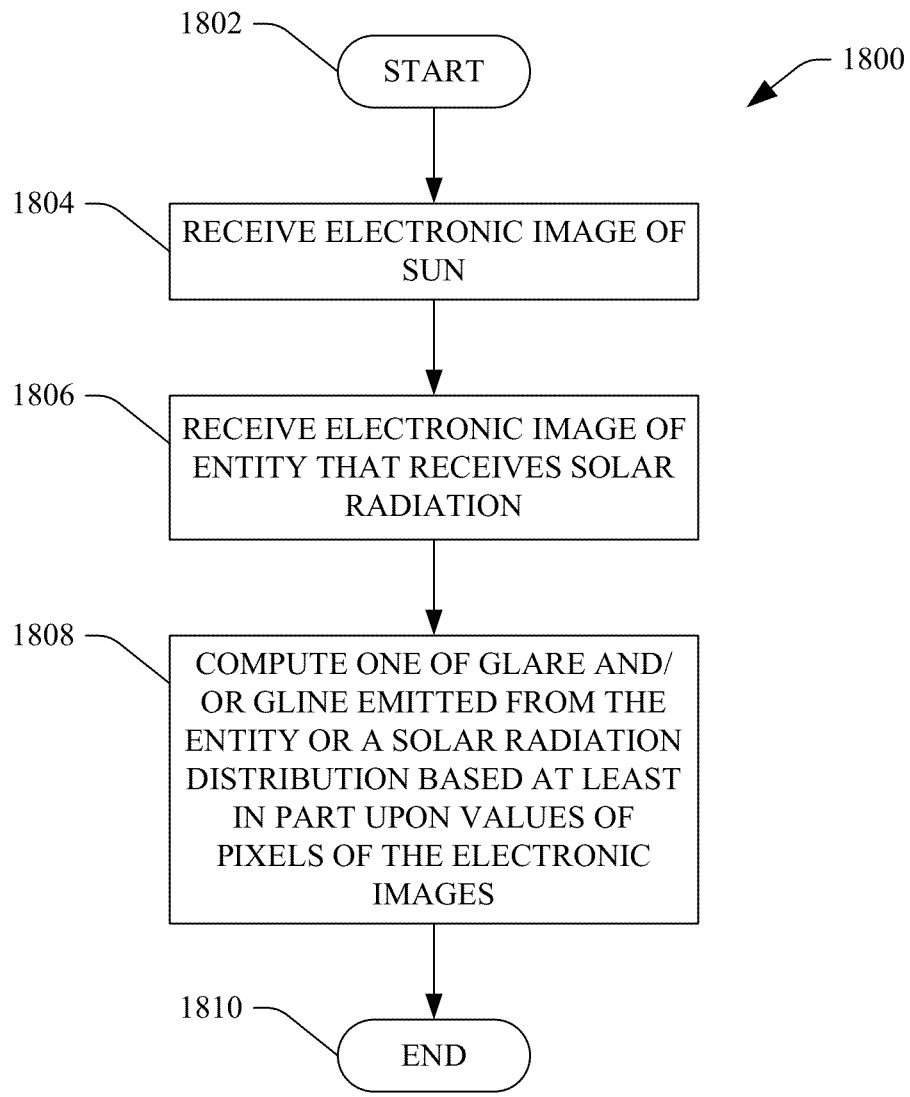
FIG. 18 is a flow diagram that illustrates an exemplary methodology for computing one of glint and/or glare emitted from an entity or solar irradiance distribution across the surface of the entity based at least in part upon values of pixels of captured electronic images of the Sun and the entity, respectively.
Figure 19:
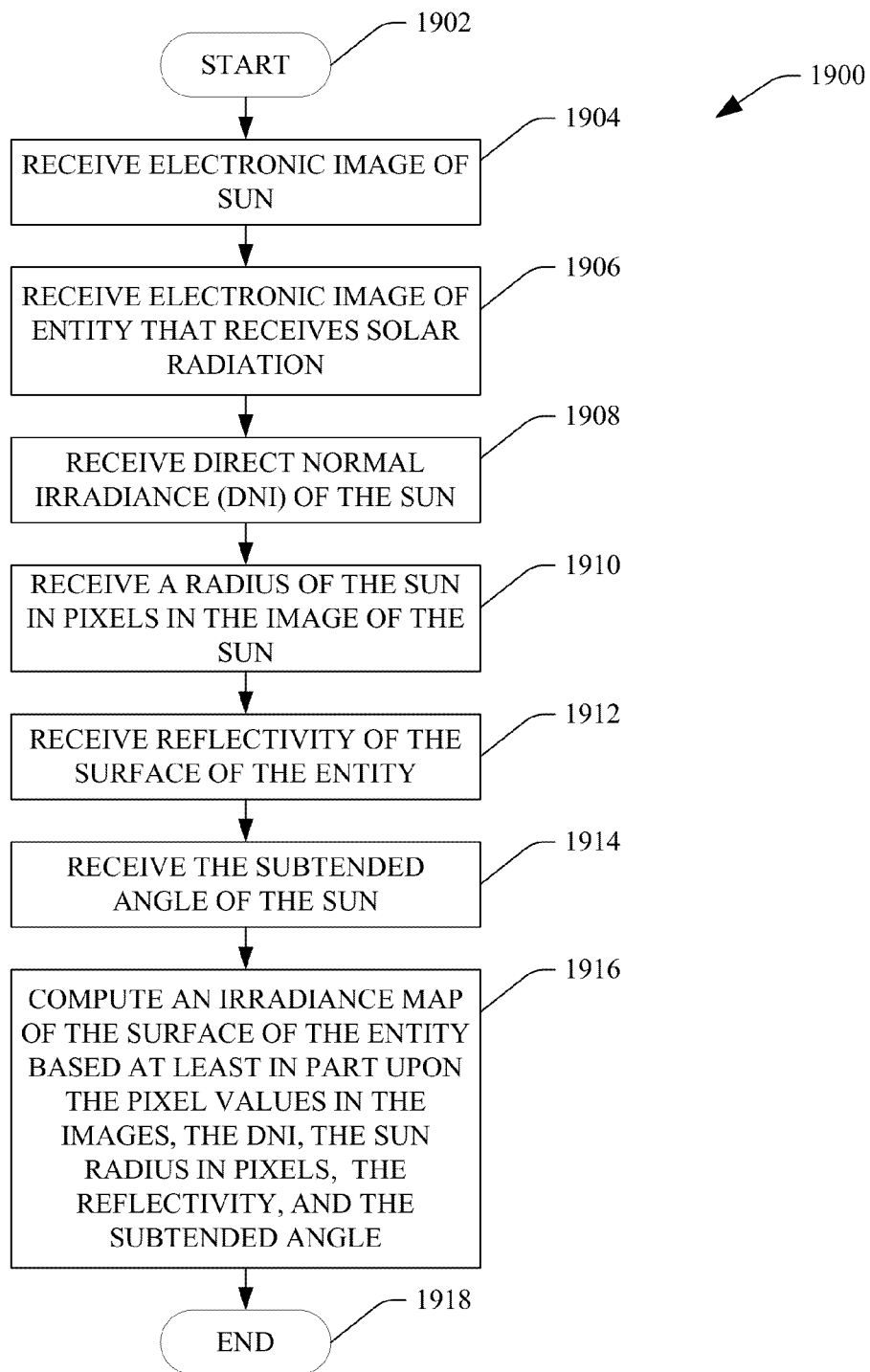
FIG. 19 is a flow diagram that illustrates an exemplary methodology for computing an irradiance map of the surface of an entity based at least in part upon pixel values of images of the Sun and the entity, respectively.
Figure 20:
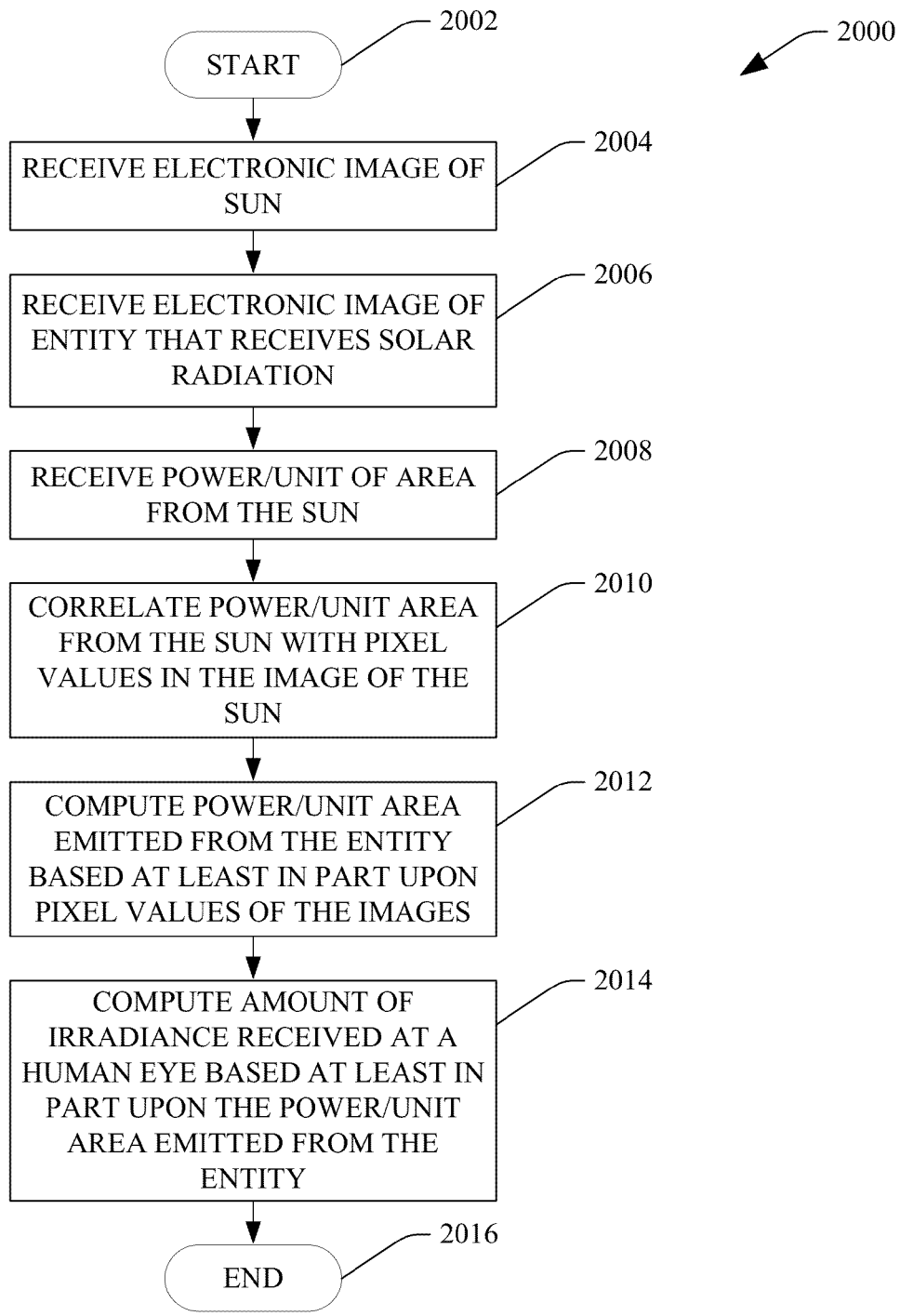
FIG. 20 is a flow diagram that illustrates an exemplary methodology for computing an amount of power received from a human eye that is reflected from a reflective entity based at least in part upon pixel values of an electronic image of the Sun and an electronic image of the reflective entity, respectively.

With reference now to FIGS. 18-20, various exemplary methodologies are illustrated and described. While the methodologies are described as being a series of acts that are performed in a sequence, it is to be understood that the methodologies are not limited by the order of the sequence. For instance, some acts may occur in a different order than what is described herein. In addition, an act may occur concurrently with another act. Furthermore, in some instances, not all acts may be required to implement a methodology described herein.

Moreover, the acts described herein may be computer-executable instructions that can be implemented by one or more processors and/or stored on a computer-readable medium or media. The computer-executable instructions may include a routine, a sub-routine, programs, a thread of execution, and/or the like. Still further, results of acts of the methodologies may be stored in a computer-readable medium, displayed on a display device, and/or the like. The computer-readable medium may be any suitable computer-readable storage device, such as memory, hard drive, CD, DVD, flash drive, or the like. As used herein, the term "computer-readable medium" is not intended to encompass a propagated signal.

With reference now to FIG. 18, an exemplary methodology 1800 that facilitates computing at least one of a solar irradiance distribution over a surface area of a receiver in a concentrating solar power system or glint and/or glare emitted from a reflective entity is illustrated. The methodology 1800 starts at 1802, and at 1804 an electronic image of the Sun is received, wherein the electronic image of the Sun comprises a first plurality of pixels that have a first plurality of intensity values.

At 1806, an electronic image of an entity that receives solar radiation is received, wherein the electronic image of the entity comprises a second plurality of pixels that have a second plurality of intensity values. At 1808, a processor is caused to compute at least one of a solar irradiance distribution over a surface of the entity captured in the electronic image of the entity that receives the solar radiation or a metric that is indicative of glare emitted from the entity based at least in part upon the first plurality of values and the second plurality of values. The methodology 1800 completes at 1810.

With reference now to FIG. 19, an exemplary methodology 1900 that facilitates computing solar irradiance distribution across a surface area of a receiver in a concentrating solar power system is illustrated. The methodology 1900 starts at 1902, and at 1904 an electronic image of the Sun is received, wherein the electronic image of the Sun comprises a first plurality of pixels that have a first plurality of intensity values.

At 1906, an electronic image of an entity that receives concentrated solar radiation is received, wherein the electronic image of the entity comprises a second plurality of pixels having a second plurality of intensity values.

At 1908, a direct normal irradiance (DNI) of the Sun is received. This can be received, for instance, from a sensor that is on-site at the solar power tower.

At 1910, a radius of the Sun in pixels in the image of the Sun is received or computed. For instance, a user can manually indicate, on the electronic image of the Sun, the radius of the Sun in pixels. Alternatively, automated image processing functions can be utilized to recognize the boundaries of the Sun in the electronic image of the Sun and can automatically determine a radius of the Sun in pixels.

At 1912, reflectivity of the surface of the entity is received. For instance, this can be computed as has been described above or can be estimated based upon material properties of the entity.

At 1914, the angle that is subtended by the Sun is received, and at 1916 an irradiance distribution across the surface of the entity is computed based at least in part upon the values of the pixels in the electronic image of the Sun and the electronic image of the entity, as well as the DNI, the radius of the Sun in pixels, the reflectivity of the entity, and the angle subtended by the Sun. The methodology 1900 completes at 1918.

With reference now to FIG. 20, an exemplary methodology 2000 for computing ocular irradiance is illustrated. The methodology 2000 starts at 2002, and at 2004 an electronic image of the Sun is received that comprises a first plurality of pixels having a first plurality of values.

At 2006, an electronic image of an entity that receives solar radiation is received, wherein the electronic image of the entity has a second plurality of pixels having a second plurality of values.

At 2008, a power per unit of area emitted from the Sun is received. For instance, this value can be known. At 2010, the power per unit area from the Sun is correlated with the pixel values in the image of the Sun. At 2012, power per unit area emitted from the entity is computed based at least in part upon the values of the pixels in the image of the Sun and the values of pixels in the image of the entity.

At 2014, an amount of irradiance received through the pupil of the human eye is computed, based at least in part upon the power per unit area that is computed at 2012. The methodology 2000 completes at 2016.

Figure 21:
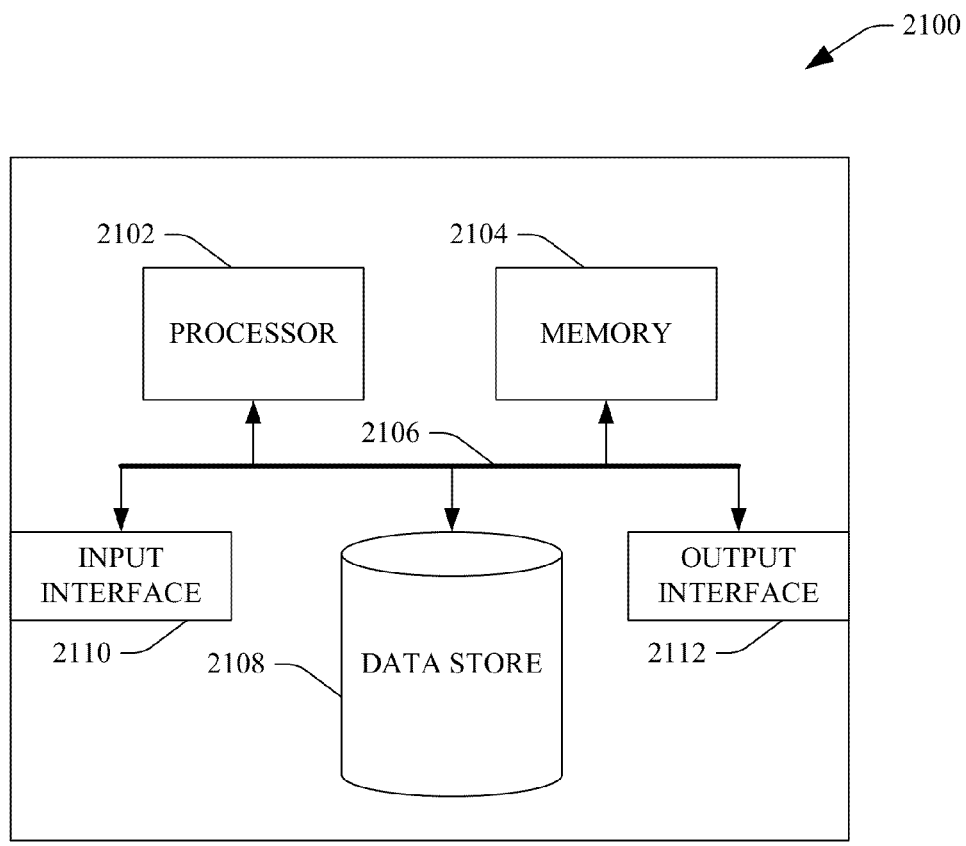
FIG. 21 is an exemplary computing system.

Now referring to FIG. 21, a high-level illustration of an exemplary computing device 2100 that can be used in accordance with the systems and methodologies disclosed herein is illustrated. For instance, the computing device 2100 may be used in a system that supports computing an irradiance distribution across the surface of a central receiver in a solar power tower. In another example, at least a portion of the computing device 2100 may be used in a system that supports computing glint and/or glare emitted from a reflective entity. The computing device 2100 includes at least one processor 2102 that executes instructions that are stored in a memory 2104. The memory 2104 may be or include RAM, ROM, EEPROM, Flash memory, or other suitable memory. The instructions may be, for instance, instructions for implementing functionality described as being carried out by one or more components discussed above or instructions for implementing one or more of the methods described above. The processor 2102 may access the memory 2104 by way of a system bus 2106. In addition to storing executable instructions, the memory 2104 may also store images, pixel values, irradiance maps, reflectivity values, etc.

The computing device 2100 additionally includes a data store 2108 that is accessible by the processor 2102 by way of the system bus 2106. The data store 2108 may be or include any suitable computer-readable storage, including a hard disk, memory, etc. The data store 2108 may include executable instructions, electronic images, reflectivity values, etc. The computing device 2100 also includes an input interface 2110 that allows external devices to communicate with the computing device 2100. For instance, the input interface 2110 may be used to receive instructions from an external computer device, a user, etc. The computing device 2100 also includes an output interface 2112 that interfaces the computing device 2100 with one or more external devices. For example, the computing device 2100 may display text, images, etc. by way of the output interface 2112.

Additionally, while illustrated as a single system, it is to be understood that the computing device 2100 may be a distributed system. Thus, for instance, several devices may be in communication by way of a network connection and may collectively perform tasks described as being performed by the computing device 2100.

It is noted that several examples have been provided for purposes of explanation. These examples are not to be construed as limiting the hereto-appended claims. Additionally, it may be recognized that the examples provided herein may be permutated while still falling under the scope of the claims.

What is claimed is:

1. A method, comprising:
   receiving an electronic image of the Sun that comprises a first plurality of pixels that have a first plurality of values;
   receiving an electronic image of an entity that receives solar radiation that comprises a second plurality of pixels that have a second plurality of values; and
   causing a processor to compute
   a solar irradiance distribution over a surface of the entity captured in the electronic image of the entity that receives the solar radiation based at least in part upon the first plurality of values and the second plurality of values;
   wherein the solar irradiance distribution over the surface of the entity comprises a plurality of computed irradiance values that correspond to the second plurality of pixels, and further comprising utilizing the following algorithm to compute the plurality of irradiance values:

$$E_{R,i} = \frac{V_{CCD,i} E_{DNI}}{\rho_{R,i} \tan^2\left(\frac{\gamma}{2}\right)} \frac{\pi r_{sun\_pixels}^2}{\sum_{sun} V_{CCD\_sun,i}},$$

where $E_{R,i}$ is an irradiance value for the surface of the entity that corresponds to pixel i in the electronic image of the entity, $V_{CCD,i}$ is a value of pixel i in the electronic image of the entity, $E_{DNI}$ is the direct normal irradiance at a time that the electronic image of the Sun was captured, $r_{sun\_pixels}$ is a number of pixels in the radius of the Sun captured in the electronic image of the Sun, $\rho_{R,i}$ is a measurement of reflectivity at a location on the surface that corresponds to pixel i in the electronic image of the entity, $\gamma$ is the angle subtended by the Sun, and $V_{CCD\_sun,i}$ is a value of pixel i in the electronic image of the Sun.

2. The method of claim 1, wherein the entity is a receiver in a solar power system.

3. The method of claim 2, wherein the entity is one of a heliostat, a parabolic trough, or a dish collector.

4. The method of claim 1, wherein the processor is caused to compute the metric that is indicative of glare emitted from the entity.

5. The method of claim 1, further comprising:
receiving a value that is indicative of reflectivity of the entity; and
causing the processor to compute the solar irradiance distribution over the surface of the entity captured in the electronic image of the entity that receives the solar radiation based at least in part upon the value that is indicative of reflectivity of the entity.

6. The method of claim 5, further comprising:
calculating the value that is indicative of the reflectivity of the entity.

7. The method of claim 6, wherein calculating the value that is indicative of the reflectivity of the entity further comprises:
receiving an electronic image of the entity without solar radiation being directed thereon that comprises a third plurality of pixels that have a third plurality of values; and
calculating values that are indicative of spatial distribution of reflectivity of the entity based at least in part upon known reflectivity of a coupon that is captured in the image of the entity.

8. The method of claim 7, wherein calculating the value that is indicative of the reflectivity of the entity further comprises:
calculating values that are indicative of spatial distribution of reflectivity of the entity based at least in part upon known reflectivity of a coupon that is captured in the image of the entity.

9. The method of claim 1 configured for execution on a mobile telephone.

10. The method of claim 1, wherein the solar irradiance distribution over the surface of the entity comprises a plurality of computed irradiance values that correspond to the second plurality of pixels, and further comprising:
outputting an electronic notification based at least in part upon a subset of the plurality of computed irradiance values.

11. The method of claim 10, wherein the electronic notification is output based at least in part upon a computed gradient amongst the plurality of irradiance values.

12. The method of claim 1, wherein at least one of the electronic image of the entity or the electronic image of the Sun is received from a video camera.

* * * * *